US012336684B2

(12) United States Patent
Mino et al.

(10) Patent No.: US 12,336,684 B2
(45) Date of Patent: Jun. 24, 2025

(54) AI-BASED ENDOSCOPIC TISSUE ACQUISITION PLANNING

(71) Applicant: OLYMPUS CORPORATION, Tokyo (JP)

(72) Inventors: Hiroyuki Mino, Westborough, MA (US); Anthony R. Pirozzi, Raleigh, NC (US); Gloria Yee, Wellesley, MA (US); Kenji Murakami, Hino (JP); Seiichiro Sakaguchi, Akishima (JP); Makoto Ishikake, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 97 days.

(21) Appl. No.: 18/315,809

(22) Filed: May 11, 2023

(65) Prior Publication Data
US 2023/0363621 A1    Nov. 16, 2023

Related U.S. Application Data

(60) Provisional application No. 63/364,566, filed on May 12, 2022.

(51) Int. Cl.
*A61B 34/10*    (2016.01)
*A61B 1/00*    (2006.01)
*A61B 10/04*    (2006.01)
*A61B 1/018*    (2006.01)
(Continued)

(52) U.S. Cl.
CPC .... *A61B 1/000096* (2022.02); *A61B 1/00006* (2013.01); *A61B 10/04* (2013.01); *A61B 1/018* (2013.01); *A61B 2017/00358* (2013.01); *A61B 2034/107* (2016.02); *A61B 2034/301* (2016.02)

(58) Field of Classification Search
CPC .......... A61B 1/000096; A61B 1/00006; A61B 10/04; A61B 2034/107; A61B 2034/301; A61B 34/10
See application file for complete search history.

(56) References Cited

U.S. PATENT DOCUMENTS

| 2018/0049643 | A1* | 2/2018 | Balog | H01J 49/068 |
| 2023/0043645 | A1* | 2/2023 | Protsenko | A61B 1/31 |
| 2023/0157762 | A1* | 5/2023 | Braido | A61B 34/37 |
| | | | | 600/424 |

FOREIGN PATENT DOCUMENTS

WO    WO-2022251715 A2 *  12/2022    ............. A61B 34/10

* cited by examiner

*Primary Examiner* — Rochelle D Turchen
(74) *Attorney, Agent, or Firm* — Schwegman Lundberg & Woessner, P.A.

(57) ABSTRACT

Systems, devices, and methods for planning an endoscopic tissue acquisition procedure for acquiring tissue from an anatomical target are disclosed. An endoscopic system comprises a steerable elongate instrument and a processor. The steerable elongate instrument can be positioned and navigated in a patient anatomy and acquire tissue from an anatomical target via a biopsy tool associated with the steerable elongate instrument. The processor can receive an image of the anatomical target, apply the received image to a trained machine-learning (ML) model to determine a tissue acquisition plan that includes a recommended biopsy tool and operational parameters for navigating the steerable elongate instrument or maneuvering the recommended biopsy tool. The tissue acquisition plan can be presented to a user, or used to facilitate a robot-assisted tissue acquisition procedure.

20 Claims, 13 Drawing Sheets

(51) Int. Cl.
*A61B 17/00* (2006.01)
*A61B 34/30* (2016.01)

AI-BASED ENDOSCOPIC TISSUE ACQUISITION PLANNING

CROSS REFERENCE TO RELATED APPLICATIONS

This application is based upon and claims the benefit of priority from U.S. Provisional Patent Application Ser. No. 63/364,566, filed on May 12, 2022, which is related to commonly assigned U.S. Provisional Patent Application Ser. No. 63/263,711, entitled "IMAGE GUIDANCE DURING CANNULATION", filed on Nov. 8, 2021, U.S. Provisional Patent Application Ser. No. 63/263,715, entitled "PROCEDURE GUIDANCE FOR SAFETY", filed on Nov. 8, 2021, U.S. Provisional Patent Application Ser. No. 63/263,720, entitled "ENDOLUMINAL TRANSHEPATIC ACCESS PROCEDURE", filed on Nov. 8, 2021, U.S. Provisional Patent Application Ser. No. 63/263,732, entitled "AUTOMATIC POSITIONING AND FORCE ADJUSTMENT IN ENDOSCOPY", filed on Nov. 8, 2021, U.S. Provisional Patent Application Ser. No. 63/363,446, entitled "AUTOMATIC POSITIONING AND FORCE ADJUSTMENT IN ENDOSCOPY", filed on Apr. 22, 2022, U.S. Provisional Patent Application Ser. No. 63/364,453, entitled "AI-BASED ENDOSCOPIC TARGET IDENTIFICATION AND PROCEDURE PLANNING", filed on May 10, 2022, U.S. Provisional patent application Ser. No. 63/364,564, entitled "RISK MANAGEMENT OF ADVERSE EVENTS IN ENDOSCOPY", filed on May 12, 2022, which are incorporated by reference in their entirety.

FIELD OF THE DISCLOSURE

The present document relates generally to endoscopic systems, and more particularly to systems and methods for computer-assisted endoscopic tissue acquisition planning using artificial intelligence.

BACKGROUND

Endoscopes have been used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices or biological matter collection devices for sampling or treating an anatomical region, and providing suction passageways for collecting fluids (e.g., saline or other preparations), among other procedures. Examples of such anatomical region can include gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

Some endoscopes include a working channel through which an operator can perform suction, placement of diagnostic or therapeutic devices (e.g., a brush, a biopsy needle or forceps, a stent, a basket, or a balloon), or minimally invasive surgeries such as tissue sampling or removal of unwanted tissue (e.g., benign or malignant strictures) or foreign objects (e.g., calculi). Some endoscopes can be used with a laser or plasma system to deliver energy to an anatomical target (e.g., soft or hard tissue or calculi) to achieve desired treatment. For example, laser has been used in applications of tissue ablation, coagulation, vaporization, fragmentation, and lithotripsy to break down calculi in kidney, gallbladder, ureter, among other stone-forming regions, or to ablate large calculi into smaller fragments.

In conventional endoscopy, the distal portion of the endoscope can be configured for supporting and orienting a therapeutic device, such as with the use of an elevator. In some systems, two endoscopes can work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

Peroral cholangioscopy is a technique that permits direct endoscopic visualization, diagnosis, and treatment of various disorders of patient biliary and pancreatic ductal system using miniature endoscopes and catheters inserted through the accessory port of a duodenoscope. Peroral cholangioscopy can be performed by using a dedicated cholangioscope that is advanced through the accessory channel of a duodenoscope, as used in Endoscopic Retrograde Cholangio-Pancreatography (ERCP) procedures. ERCP is a technique that combines the use of endoscopy and fluoroscopy to diagnose and treat certain problems of the biliary or pancreatic ductal systems, including the liver, gallbladder, bile ducts, pancreas, or pancreatic duct. In ERCP, an cholangioscope (also referred to as an auxiliary scope, or a "daughter" scope) can be attached to and advanced through a working channel of a duodenoscope (also referred to as a main scope, or a "mother" scope). Typically, two separate endoscopists operate each of the "mother-daughter" scopes. Although biliary cannulation can be achieved directly with the tip of the cholangioscope, most endoscopists prefer cannulation over a guidewire. A tissue retrieval device can be inserted through the cholangioscope to retrieve biological matter (e.g., gallstones, bill duct stones, cancerous tissue) or to manage stricture or blockage in bile duct.

In ERCP, the duodenoscope can be passed through the mouth and esophagus and down to the duodenum, access the papilla of Vater in the duodenum. Contrast dyes can be injected through the papilla into the ductal system, and fluoroscopic images taken to show lesions, stones, strictures or blockages. One treatment involving the use of ERCP is sphincterotomy, which involves making a small cut in the papilla of Vater to enlarge the opening of the bile duct and/or pancreatic duct to improve the drainage or to remove biliary ductal calculi. Another ERCP treatment involves placing a stricture management device (e.g., a stent) in a blocked or narrowed duct portion to improve drainage or to facilitate passing a device therethrough. Yet another ERCP treatment is tissue acquisition, such as a biopsy to remove samples for pathology assessment.

Peroral cholangioscopy can also be performed by inserting a small-diameter dedicated endoscope directly into the bile duct, such as in a Direct Per-Oral Cholangioscopy (DPOC) procedure. In DPOC, a slim endoscope (cholangioscope) can be inserted into patient mouth, pass through the upper GI tract, and enter into the common bile duct for visualization, diagnosis, and treatment of disorders of the biliary and pancreatic ductal systems.

SUMMARY

The present disclosure recognizes several technological problems to be solved with conventional endoscopes, such as duodenoscopes used for diagnostics and retrieval of sample biological matter. One of such problems is increased difficulty in navigating endoscopes, and instruments inserted therein, to locations in anatomical regions deep within a patient. For example, in ERCP procedures, as the duodenoscope, the cholangioscope, and the tissue retrieval device become progressively smaller due to being inserted sequentially in progressively smaller lumens, it has become more difficult to maneuver and navigate the endoscope through the patient anatomy, maintain endoscope stabilization, and maintain correct cannulation position in a narrow space (e.g., the bile duct). It can also be difficult to maintain an appropriate cannulation angle due to limited degree of freedom in scope elevator. Cannulation and endoscope navigation require advanced surgical skills and manual dexterity, which can be particularly challenging for less-experienced operating physicians (e.g., surgeons or endoscopists).

The difficulty in cannulation and endoscope navigation may also be attributed to variability of patient anatomy, especially patients with surgically altered or otherwise difficult anatomy. For example, in ERCP procedures, some patients may have altered anatomy to a portion of the GI tract or the pancreaticobiliary system (e.g., the ampulla). In some patients, stricture ahead of pancreas can compress the stomach and part of duodenum, making it difficult to navigate the duodenoscope in a limited lumen of the compressed duodenum and to navigate the cholangioscope to reach the duodenal papilla, the point where the dilated junction of the pancreatic duct and the bile duct (ampulla of Vater) enter the duodenum. In another example, some patients have alternated papilla anatomy. With the duodenoscope designed to be stable in the duodenum, it can be more difficult to reach the duodenal papilla in surgically altered anatomy.

Another identified problem of conventional endoscopic system, in its application of tissue acquisition or biopsy procedures, is a lack of capability of automatic or computer-assisted tissue acquisition planning tailored for individual patients depending on their respective anatomies and medical conditions. One goal of endoscopic tissue acquisition procedure is to acquire a sufficient amount of biopsy tissue in one biopsy procedure. Needle, knife, and biopsy forceps are the most commonly used tissue acquisition tools in ERCP, while other tools are available, including brushes, snares, and suction devices. Proper tissue acquisition planning, such as determining suitable tools and proper operation and navigation of such tools, is crucial for effective and efficient tissue collection, especially in a robot-assisted tissue acquisition procedure. Conventional endoscopic tissue acquisition procedures generally rely on manual procedure planning (e.g., the physician selects biopsy tools and decides manner of operating such tools in a procedure like ERCP), which can be time consuming and heavily dependent on endoscopists' experience and skills. For example, to determine a proper tissue acquisition tool, the physician needs to take into consideration a multitude of factors including size, characteristics, and location of the target tissue, its neighboring environment, local conditions at the surgical site (e.g., tissue inflammation), and patient general health status, among others. For inexperienced physicians or endoscopists, it can be challenging to determine what tools to use and how to best manipulate such tools to maximize the amount of tissue collected while minimizing complications and preserving tissue functionality at the acquisition site, especially in patients with surgically altered or otherwise difficult anatomy.

The present disclosure can help solve these and other problems by providing systems, devices and method for automatic tissue acquisition planning in an endoscopic procedure such as ERCP. Artificial intelligence (AI) or machine learning (ML) may be used to automate and optimize the process of tissue acquisition planning, such as identifying suitable tools and proper manipulation of such tools and/or navigation of an endoscope over which the tools are deployed, and estimating the amount of biopsy tissue to be collected using such tools. According to one embodiment, an endoscopic system comprises a steerable elongate instrument and a processor. The steerable elongate instrument can be positioned and navigated in a patient anatomy and acquire tissue from an anatomical target via a biopsy tool associated with the steerable elongate instrument. The processor can be configured to receive patient information including an image of the anatomical target, apply the received image of the anatomical target to a trained machine-learning (ML) model to determine a tissue acquisition plan. The tissue acquisition plan can include a recommended biopsy tool and recommended values of one or more operational parameters for navigating the steerable elongate instrument or maneuvering the recommended biopsy tool to maximize an amount of collected tissue. The tissue acquisition plan can be presented on a user interface as a peri-operative guidance to assist the operating physician during the procedure. In some examples, the system can include a controller configured to control an actuator to robotically facilitate an operation of the steerable elongate instrument or a biopsy tool associated therewith (e.g., the recommended biopsy tool) in a tissue acquisition procedure.

The AI-based tissue acquisition planning, including automated process of identifying tissue acquisition tools and estimating an amount of biopsy tissue to be collected, can improve the efficiency of tissue acquisition and operation reliability. This can be especially desirable in a robot-assisted endoscopic procedure. Enhanced automation in endoscopic procedure can help ease the burden manual surgical planning, reduce variability of procedure outcome due to variations in experience and dexterity across operating physicians (e.g., surgeons or endoscopists), and improve the endoscopic procedure prognostic predictability. As a result, overall procedure efficiency, accuracy, patient safety, and endoscopic procedure success rate can be improved.

Example 1 is an endoscopic system, comprising: a steerable elongate instrument configured to be positioned and navigated in a patient anatomy, and to acquire tissue from an anatomical target via a biopsy tool associated with the steerable elongate instrument; and a processor configured to: receive patient information including an image of the anatomical target; apply the received image of the anatomical target to a trained machine-learning (ML) model to generate an endoscopic tissue acquisition plan for acquiring the tissue from the anatomical target; and output the generated endoscopic tissue acquisition plan.

In Example 2, the subject matter of Example 1 optionally includes a user interface configured to present the image of the anatomical target and the generated endoscopic tissue acquisition plan to a user.

In Example 3, the subject matter of Example 2 optionally includes the user interface that can be configured to receive a user input designating one or more biopsy locations at the anatomical target; and the processor is configured to register the one or more biopsy locations, and to identify one or more biopsied tissues collected therefrom by their respective biopsy locations.

In Example 4, the subject matter of any one or more of Examples 1-3 optionally includes a controller configured to provide a control signal to an actuator to robotically facilitate a navigation of the steerable elongate instrument and a manipulation of the biopsy tool to acquire the tissue in accordance with the endoscopic tissue acquisition plan.

In Example 5, the subject matter of any one or more of Examples 1-4 optionally includes the processor that can be configured to use the trained ML model to generate the endoscopic tissue acquisition plan including a recommended biopsy tool of a specific type or size for use in a tissue acquisition procedure.

In Example 6, the subject matter of Example 5 optionally includes the recommended biopsy tool that can include one of a brush, a snare, forceps, or a suction device.

In Example 7, the subject matter of Example 6 optionally includes the recommended biopsy tool that can include a braided snare device sized and shaped to enhance gripping of biopsied tissue.

In Example 8, the subject matter of any one or more of Examples 5-7 optionally includes the processor that can be configured to use the trained ML model to generate the endoscopic tissue acquisition plan including to determine one or more operational parameters for navigating the steerable elongate instrument or maneuvering the recommended biopsy tool to maximize an amount of tissue collected from the anatomical target.

In Example 9, the subject matter of Example 8 optionally includes the processor that can be configured to estimate the amount of tissue to be collected by the recommended biopsy tool based on the one or more operational parameters thereof.

In Example 10, the subject matter of any one or more of Examples 8-9 optionally includes the determined one or more operational parameters that can include a position, a posture, a heading direction, or an angle of the biopsy tool relative to the anatomical target.

In Example 11, the subject matter of any one or more of Examples 8-10 optionally includes the determined one or more operational parameters that can include a navigation path for navigating the steerable elongate instrument or maneuvering the recommended biopsy tool to the anatomical target.

In Example 12, the subject matter of any one or more of Examples 1-11 optionally includes the processor that can be configured to use the trained ML model to generate the endoscopic tissue acquisition plan including to determine a recommended amount of tissue to be collected from the anatomical target.

In Example 13, the subject matter of Example 12 optionally includes the generated endoscopic tissue acquisition plan that can include multiple acquisition steps and recommended respective amounts of tissue to be collected at each of the multiple acquisition steps.

In Example 14, the subject matter of any one or more of Examples 1-13 optionally includes the processor that can include a training module configured to train an ML model using a training dataset comprising procedure data from past endoscopic biopsy procedures on a plurality of patients, the procedure data including (i) images of anatomical targets of the plurality of patients and (ii) assessments of tissue acquisition plans corresponding to the images of anatomical targets.

In Example 15, the subject matter of Example 14 optionally includes the training module that can be configured to train the ML model using supervised learning or unsupervised learning.

In Example 16, the subject matter of any one or more of Examples 1-15 optionally includes the anatomical target that can include an anatomical stricture, and wherein the processor is configured to apply the endoscopic image of the anatomical stricture to the trained ML model to estimate malignancy of the anatomical stricture.

Example 17 is a method of planning an endoscopic tissue acquisition procedure for acquiring tissue from an anatomical target via an steerable elongate instrument and a biopsy tool associated therewith, the method comprising: providing patient information including an image of the anatomical target; applying the image of the anatomical target to a trained machine-learning (ML) model to generate an endoscopic tissue acquisition plan for acquiring tissue from the anatomical target; and outputting the generated endoscopic tissue acquisition plan.

In Example 18, the subject matter of Example 17 optionally includes providing a control signal to an actuator to robotically facilitate a navigation of the steerable elongate instrument and a manipulation of the biopsy tool to acquire the tissue in accordance with the endoscopic tissue acquisition plan.

In Example 19, the subject matter of any one or more of Examples 17-18 optionally includes: receiving a user input designating one or more biopsy locations at the anatomical target; registering the one or more biopsy locations; and identifying one or more biopsied tissues collected therefrom by their respective biopsy locations.

In Example 20, the subject matter of any one or more of Examples 17-19 optionally includes the generated endoscopic tissue acquisition plan that can include a recommended biopsy tool of a specific type or size for use in a tissue acquisition procedure.

In Example 21, the subject matter of Example 20 optionally includes the generated endoscopic tissue acquisition plan that can include one or more operational parameters for navigating the steerable elongate instrument or maneuvering the recommended biopsy tool to maximize an amount of tissue collected from the anatomical target.

In Example 22, the subject matter of Example 21 optionally includes the one or more operational parameters that can include one or more of: a position, a posture, a heading direction, or an angle of the biopsy tool relative to the anatomical target; or a navigation path for navigating the steerable elongate instrument or maneuvering the recommended biopsy tool to the anatomical target.

In Example 23, the subject matter of any one or more of Examples 17-22 optionally includes the generated endoscopic tissue acquisition plan that can include a recommended amount of tissue to be collected from the anatomical target.

In Example 24, the subject matter of any one or more of Examples 17-23 optionally includes, via a training module, training an ML model using a training dataset comprising procedure data from past endoscopic biopsy procedures on a plurality of patients, the procedure data including (i) images of anatomical targets of the plurality of patients and (ii) assessments of tissue acquisition plans corresponding to the images of anatomical targets.

In Example 25, the subject matter of any one or more of Examples 17-24 optionally includes the anatomical target that can include an anatomical stricture, the method further comprising applying the endoscopic image of the anatomical stricture to the trained ML model to estimate malignancy of the anatomical stricture.

Example 26 is a non-transitory machine-readable storage medium that includes instructions that, when executed by one or more processors of a machine, cause the machine to perform operations comprising: receiving patient information including an image of an anatomical target; applying the image of the anatomical target to a trained machine-learning (ML) model to generate an endoscopic tissue acquisition plan for acquiring tissue from the anatomical target; and outputting the generated endoscopic tissue acquisition plan.

In Example 27, the subject matter of Example 26 optionally include the instructions cause the machine to perform operations that can include: receiving a user input designating one or more biopsy locations at the anatomical target; registering the one or more biopsy locations; and identifying one or more biopsied tissues collected therefrom by their respective biopsy locations.

In Example 28, the subject matter of any one or more of Examples 26-27 optionally includes the generated endoscopic tissue acquisition plan that can include at least one of: a recommended biopsy tool of a specific type or size for use in a tissue acquisition procedure; one or more operational parameters for navigating a steerable elongate instrument or maneuvering the recommended biopsy tool to maximize an amount of tissue collected from the anatomical target; or a recommended amount of tissue to be collected from the anatomical target.

In Example 29, the subject matter of any one or more of Examples 26-28 optionally includes the instructions cause the machine to perform operations that can include training an ML model using a training dataset comprising procedure data from past endoscopic biopsy procedures on a plurality of patients, the procedure data including (i) images of anatomical targets of the plurality of patients and (ii) assessments of tissue acquisition plans corresponding to the images of anatomical targets.

In Example 30, the subject matter of any one or more of Examples 26-29 optionally includes the instructions cause the machine to perform operations that can include providing a control signal to an actuator to robotically facilitate a navigation of a steerable elongate instrument and a manipulation of a biopsy tool to acquire the tissue in accordance with the endoscopic tissue acquisition plan.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

DETAILED DESCRIPTION

This document describes AI-based systems, devices, and methods for planning an endoscopic tissue acquisition procedure for acquiring tissue from an anatomical target. According to one embodiment, an endoscopic system comprises a steerable elongate instrument and a processor. The steerable elongate instrument can be positioned and navigated in a patient anatomy and acquire tissue from an anatomical target via a biopsy tool associated with the steerable elongate instrument. The processor can receive patient information including an image of the anatomical target, apply the received image of the anatomical target to a trained machine-learning (ML) model to determine a tissue acquisition plan that includes a recommended biopsy tool, and recommended values of one or more operational parameters for navigating the steerable elongate instrument or maneuvering the recommended biopsy tool to maximize an amount of the collected tissue. The tissue acquisition plan can be presented to a user, or used to facilitate a robot-assisted tissue acquisition procedure.

Figure 1:
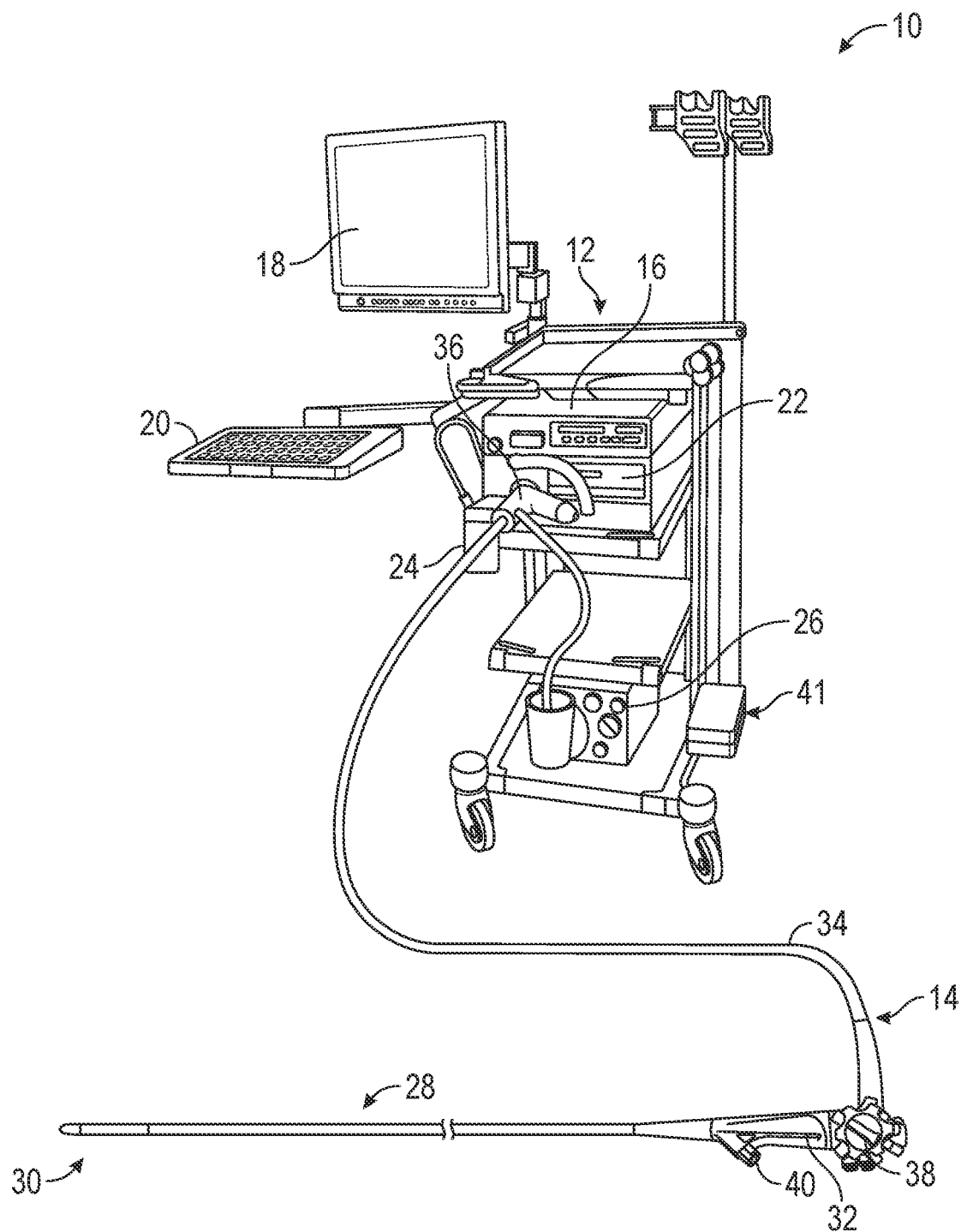
FIGS. 1-2 are schematic diagrams illustrating an example of an endoscopy system for use in endoscopic procedures such as an ERCP procedure.

FIG. 1 is a schematic diagram illustrating an example of an endoscopy system 10 for use in endoscopic procedures, such as an ERCP procedure. The system 10 comprises an imaging and control system 12 and an endoscope 14. The endoscopy system 10 is an illustrative example of an endoscopy system suitable for patient diagnosis and/or treatment using the systems, devices and methods described herein, such as tethered and optically enhanced biological matter and tissue collection, retrieval and storage devices and biopsy instruments that can be used for obtaining samples of tissue or other biological matter to be removed from a patient for analysis or treatment of the patient. According to some examples, the endoscope 14 can be insertable into an anatomical region for imaging and/or to provide passage of or attachment to (e.g., via tethering) one or more sampling devices for biopsies, or one or more therapeutic devices for treatment of a disease state associated with the anatomical region.

The imaging and control system 12 can comprise a control unit 16, an output unit 18, an input unit 20, a light source 22, a fluid source 24, and a suction pump 26. The imaging and control system 12 can include various ports for coupling with endoscopy system 10. For example, the control unit 16 can include a data input/output port for receiving data from and communicating data to the endoscope 14. The light source 22 can include an output port for transmitting light to the endoscope 14, such as via a fiber optic link. The fluid source 24 can comprise one or more sources of air, saline or other fluids, as well as associated fluid pathways (e.g., air channels, irrigation channels, suction channels) and connectors (barb fittings, fluid seals, valves and the like). The fluid source 24 can be in communication with the control unit 16, and can transmit one or more sources of air or fluids to the endoscope 14 via a port. The fluid source 24 can comprise a pump and a tank of fluid or can be connected to an external tank, vessel or storage unit. The suction pump 26 can comprise a port used to draw a vacuum from the endoscope 14 to generate suction, such as for withdrawing fluid from the anatomical region into which the endoscope 14 is inserted.

The output unit 18 and the input unit 20 can be used by a human operator and/or a robotic operator of endoscopy system 10 to control functions of endoscopy system 10 and view output of the endoscope 14. In some examples, the control unit 16 can additionally be used to generate signals or other outputs for treating the anatomical region into which the endoscope 14 is inserted. Examples of such signals or outputs can include electrical output, acoustic output, a radio-frequency energy output, a fluid output and the like for treating the anatomical region with, for example, cauterizing, cutting, freezing and the like.

The endoscope 14 can interface with and connect to the imaging and control system 12 via a coupler section 36. In the illustrated example, the endoscope 14 comprises a duodenoscope that may be use in a ERCP procedure, though other types of endoscopes can be used with the features and teachings of the present disclosure. The endoscope 14 can comprise an insertion section 28, a functional section 30, and a handle section 32, which can be coupled to a cable section 34 and the coupler section 36.

Figure 4:
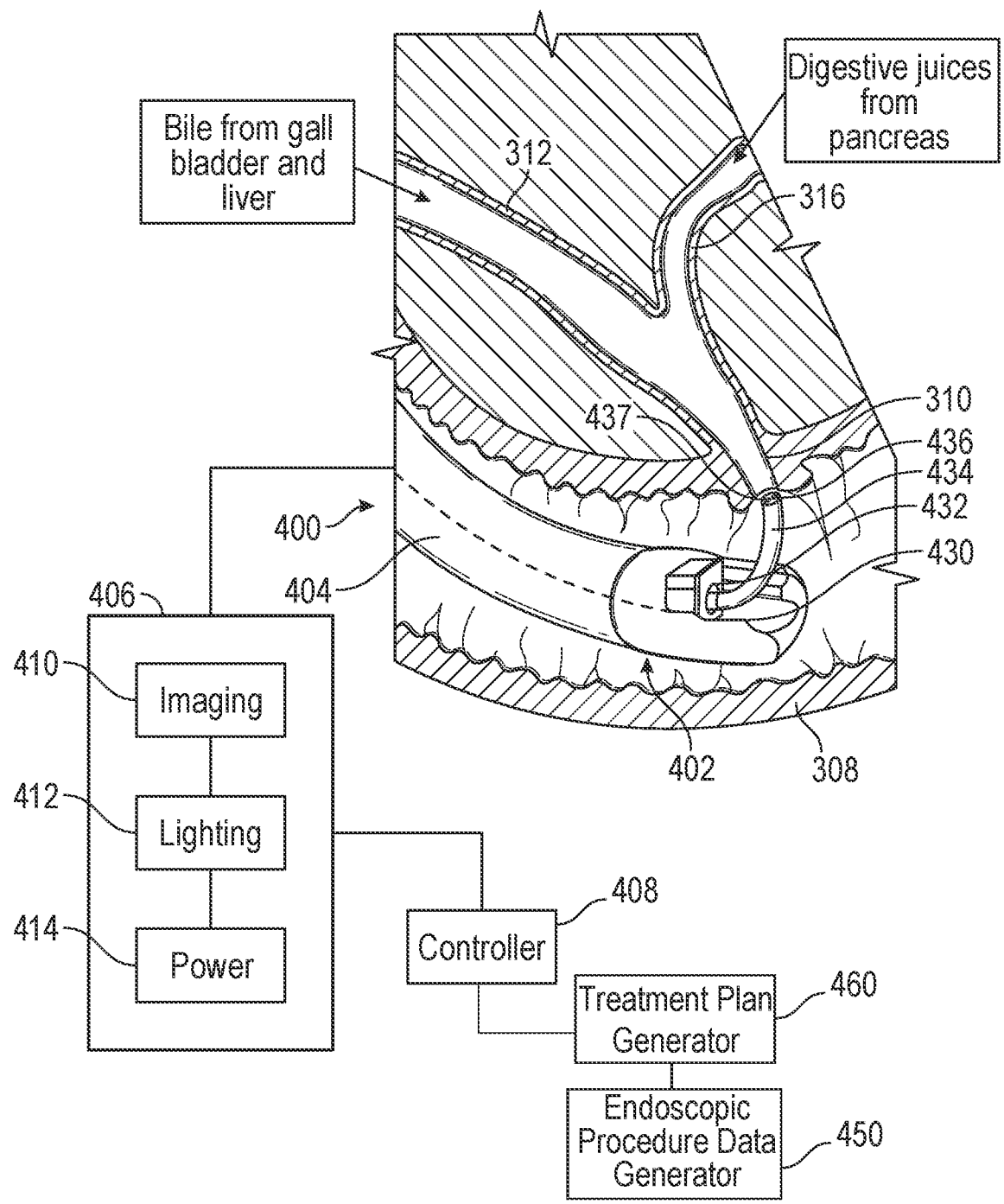
FIG. 4 is diagram illustrating an example of mother-daughter endoscopes used in ERCP and a portion of patient anatomy of the procedure site.

The insertion section 28 can extend distally from the handle section 32, and the cable section 34 can extend proximally from the handle section 32. The insertion section 28 can be elongate and include a bending section, and a distal end to which functional section 30 can be attached. The bending section can be controllable (e.g., by control knob 38 on the handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30, such as a cholangioscope as shown in FIG. 4. The working channel can extend between handle section 32 and functional section 30. Additional functionalities, such as fluid passages, guide wires, and pull wires can also be provided by insertion section 28 (e.g., via suction or irrigation passageways, and the like).

The handle section 32 can comprise a control knob 38 and ports 40. The ports 40 can be configured to couple various electrical cables, guide wires, auxiliary scopes, tissue collection devices of the present disclosure, fluid tubes and the like to handle section 32 for coupling with insertion section 28. The control knob 38 can be coupled to a pull wire, or other actuation mechanisms, extending through insertion section 28. The control knob 38 can be used by a user to manually advance or retreat the insertion section 28 of the endoscope 14, and to adjust bending of a bending section at the distal end of the insertion section 28. In some examples, an optional drive unit 46 (FIG. 2) can be used to provide motorized drive for advancing a distal section of endoscope 14 under the control of the control unit 16.

The imaging and control system 12, according to examples, can be provided on a mobile platform (e.g., cart 41) with shelves for housing light source 22, suction pump 26, image processing unit 42 (FIG. 2), etc. Alternatively, several components of the imaging and control system 12 shown in FIGS. 1 and 2 can be provided directly on the endoscope 14 such that the endoscope is "self-contained."

The functional section 30 can comprise components for treating and diagnosing anatomy of a patient. The functional section 30 can comprise an imaging device, an illumination device, and an elevator. The functional section 30 can further comprise optically enhanced biological matter and tissue collection and retrieval devices. For example, the functional section 30 can comprise one or more electrodes conductively connected to handle section 32 and functionally connected to the imaging and control system 12 to analyze biological matter in contact with the electrodes based on comparative biological data stored in the imaging and control system 12. In other examples, the functional section 30 can directly incorporate tissue collectors.

In some examples, the endoscope 14 can be robotically controlled, such as by a robot arm attached thereto. The robot arm can automatically, or semi-automatically (e.g., with certain user manual control or commands), via an actuator, position and navigate instrument such as the endoscope 14 (e.g., the functional section 30 and/or the insertion section 28) in an anatomical target, or position a device at a desired location with desired posture to facilitate an operation on the anatomical target (e.g., to acquire tissue samples from the anatomical targe using a brush, a snare, forceps, or a suction device). In accordance with various examples discussed in this document, a controller can use artificial intelligence (AI) to determine cannulation and navigation parameters and/or tool operational parameters (e.g., position, angle, posture, force, and navigation path), and generate a control signal to the actuator of the robot arm to facilitate operation of such instrument or tools in accordance with the determined navigation and operational parameters in a robot-assisted procedure.

Figure 2:
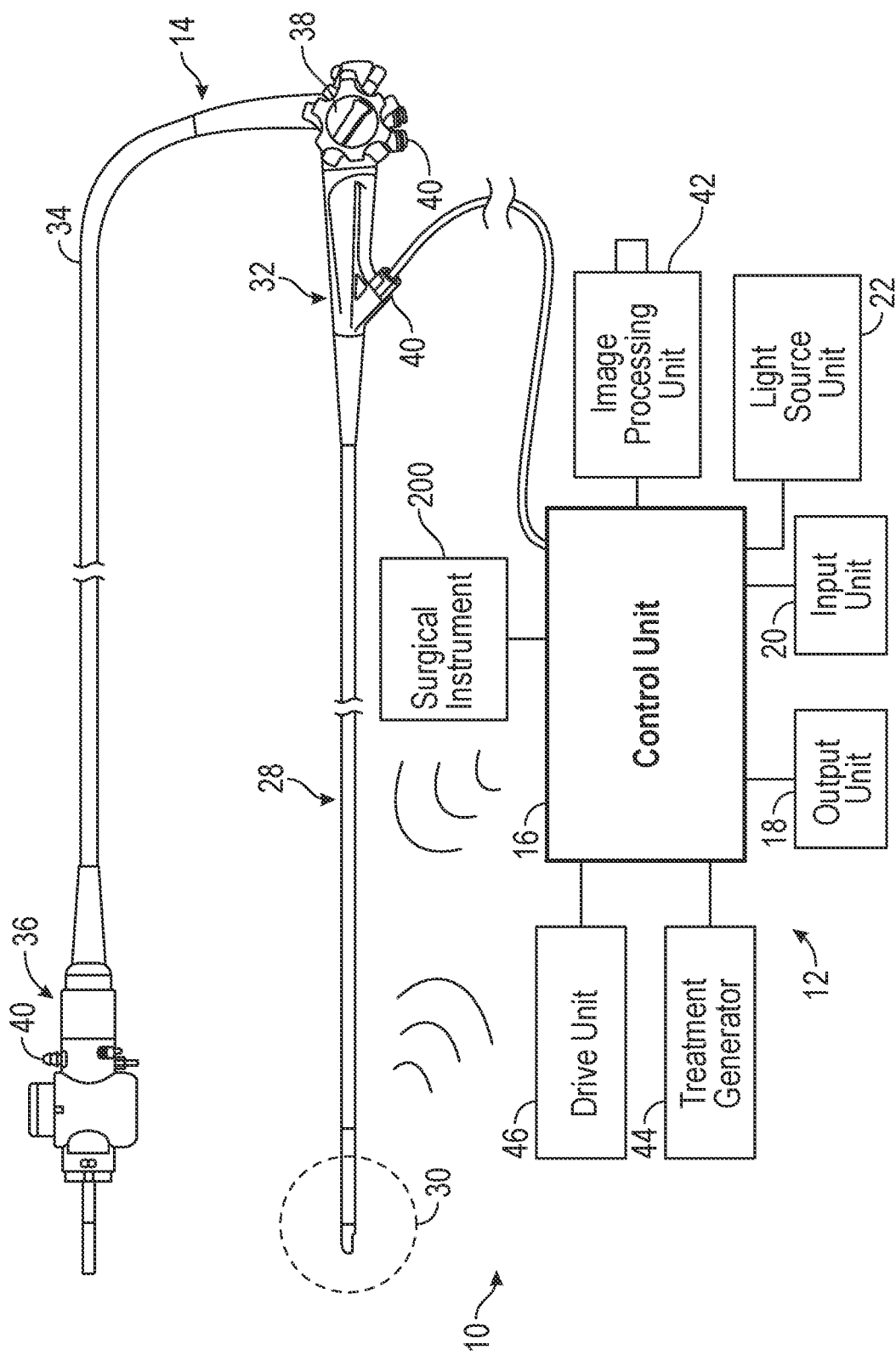

FIG. 2 is a schematic diagram of the endoscopy system 10 shown in FIG. 1, which comprises the imaging and control system 12 and the endoscope 14. FIG. 2 schematically illustrates components of the imaging and control system 12 coupled to the endoscope 14, which in the illustrated example comprises a duodenoscope. The imaging and control system 12 can comprise a control unit 16, which can include or be coupled to an image processing unit 42, a treatment generator 44, and a drive unit 46, as well as the light source 22, the input unit 20, and the output unit 18 as discussed above with reference to FIG. 1. The control unit 16 can comprise, or can be in communication with, a surgical instrument 200 comprising a device configured to engage tissue and collect and store a portion of that tissue and through which an imaging device (e.g., a camera) can view target tissue via inclusion of optically enhanced materials and components. The control unit 16 can be configured to activate an imaging device (e.g., a camera) at the functional section of the endoscope 14 to view target tissue distal of surgical instrument 200 and endoscopy system 10, which can be fabricated of a translucent material to minimize the impacts of the camera being obstructed or partially obstructed by the tissue retrieval device. Likewise, the control unit 16 can be configured to activate the light source 22 to shine light on the surgical instrument 200, which can include select components that are configured to reflect light in a particular manner, such as tissue cutters being enhanced with reflective particles.

The image processing unit 42 and the light source 22 can each interface with the endoscope 14 (e.g., at the functional section 30) by wired or wireless electrical connections. The imaging and control system 12 can accordingly illuminate an anatomical region using the light source 22, collect signals representing the anatomical region, process signals representing the anatomical region using the image processing unit 42, and display images representing the anatomical region on the output unit 18. The imaging and control system 12 can include the light source 22 to illuminate the anatomical region using light of desired spectrum (e.g., broadband white light, narrow-band imaging using preferred electromagnetic wavelengths, and the like). The imaging and control system 12 can connect (e.g., via an endoscope connector) to the endoscope 14 for signal transmission (e.g., light output from light source, video signals from the imaging device such as positioned at the distal portion of the endoscope 14, diagnostic and sensor signals from a diagnostic device, and the like).

The treatment generator 44 can generate a tissue acquisition plan, which can be provided with the operating physician as a guidance for maneuvering the endoscope 14 during a tissue acquisition procedure, or used by the control unit 16 to control the operation of the endoscope 14. In some examples, the tissue acquisition plan can include identification of suitable tissue acquisition tools, methods of operating and navigating such tools and the endoscope 14 over which the tools are deployed, and an estimation of the amount of biopsy tissue collected using such tools, among other treatment or control parameters. The treatment generator 44 can generate the tissue acquisition plan using patient information including images of the anatomical target. Examples of the images can include endoscopic images, images from external imaging devices such as X-ray or fluoroscopy images, electrical potential map or an electrical impedance map, computer tomography (CT) images, magnetic resonance imaging (MRI) images obtained in Magnetic resonance cholangiopancreatography (MRCP), or acoustic images such as endoscopic ultrasonography (EUS) images, among others. In some examples, the treatment generator 44 can identify suitable tissue acquisition tools and tool operational parameters using artificial intelligence (AI) or machine learning (ML). The tissue acquisition plan can be presented an operating physician as a guidance during the procedure. The AI-based tissue acquisition plan can assist the operating physician in precisely retrieving a desired amount of tissue while minimizing the complication and preserving functionality of the anatomy at the biopsy site. Additionally or alternatively, the tissue acquisition plan can be provided to a robotic system to facilitate used to facilitate a robot-assisted endoscopic procedure. Examples of AI-based tissue acquisition planning are discussed below with reference to FIGS. 6 and 7A-7D.

Figure 3A:
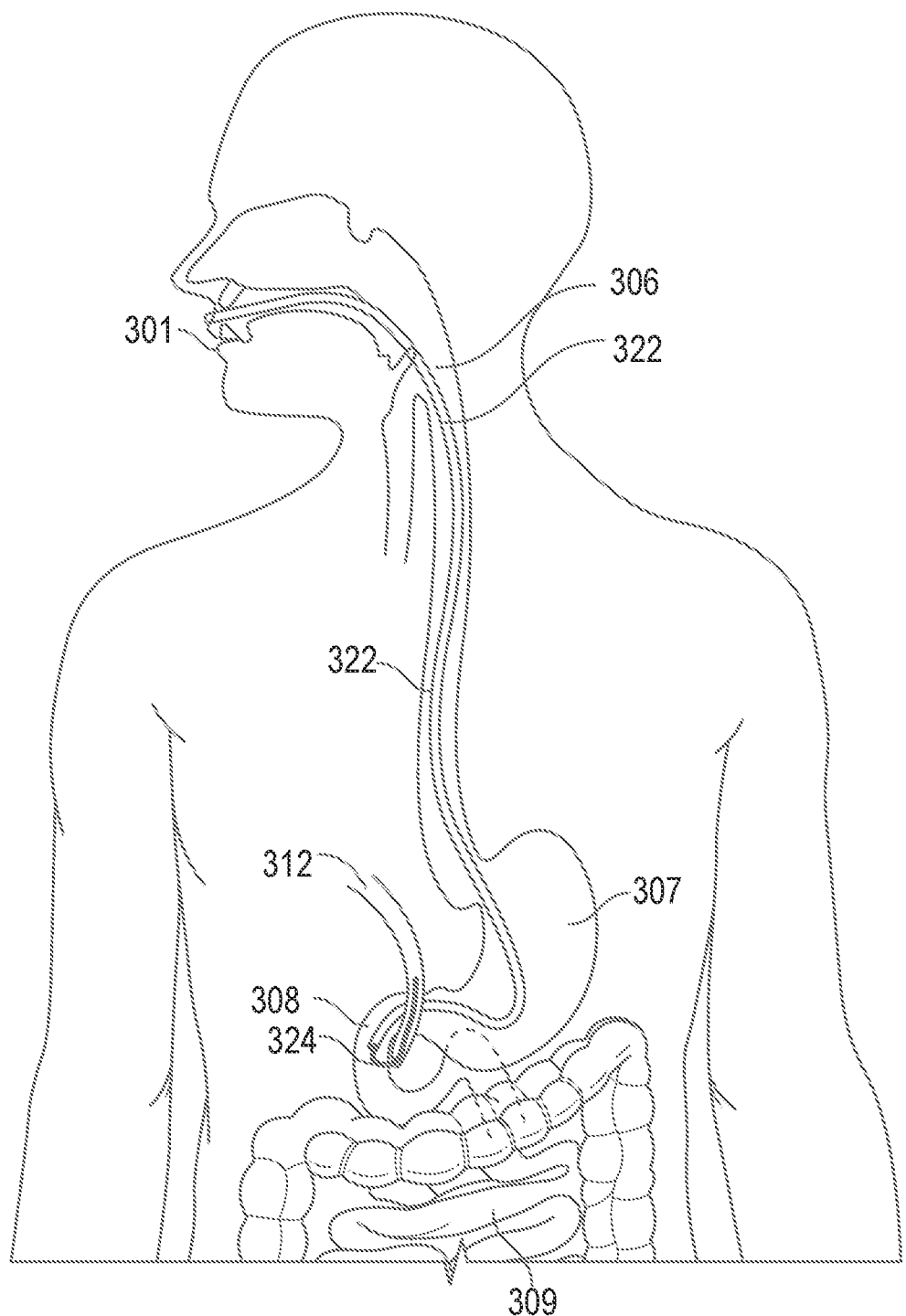
FIGS. 3A-3B are diagrams illustrating an example of peroral cholangioscopy involving direct insertion of a cholangioscope into patient bile duct as in a DPOC procedure, and a portion of patient anatomy where the procedure is performed.
Figure 3B:
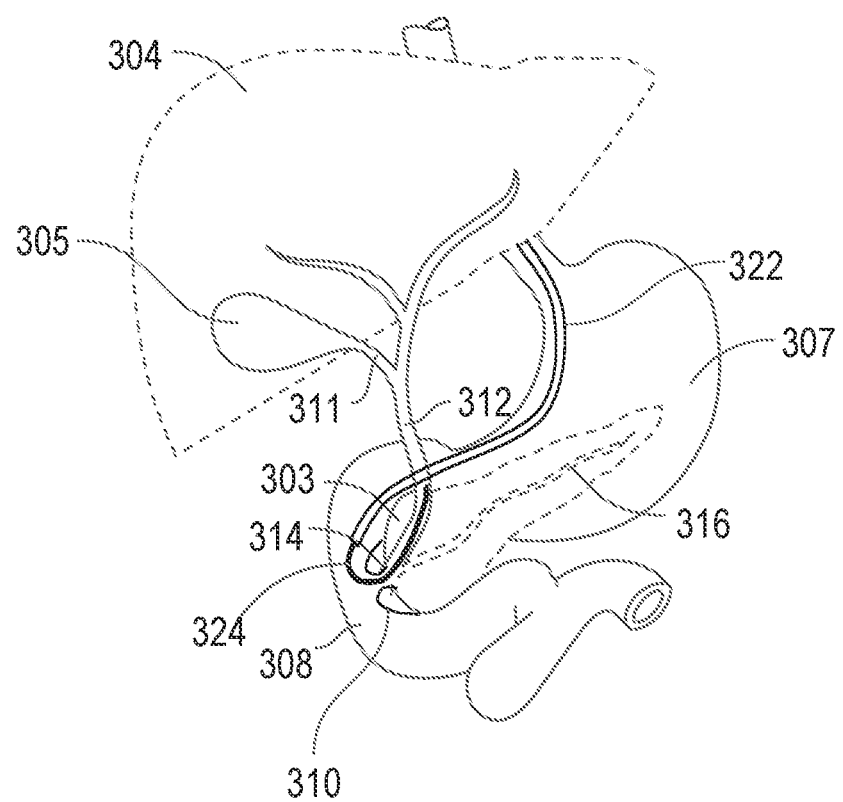

FIGS. 3A-3B are diagrams illustrating an example of peroral cholangioscopy performed via direct insertion of a cholangioscope 324 into the bile duct, as in a DPOC procedure, and a portion of patient anatomy where the procedure is performed. The cholangioscope 324 is nested inside of a guide sheath 322, and inserted perorally into a patient to reach duodenum 308. Duodenum 308 comprises an upper part of the small intestine. The guide sheath 322 can extend into mouth 301, through esophagus 306, through stomach 307 to reach the duodenum 308. Before reaching intestines 309, the guide sheath 322 can position the cholangioscope 324 proximate common bile duct 312. The common bile duct 312 carries bile from the gallbladder 305 and liver 304, and empties the bile into the duodenum 308 through sphincter of Oddi 310 (FIG. 3B). The cholangioscope 324 can extend from guide sheath 322 to extend into common bile duct 312. In some examples, steering features of guide sheath 322 (e.g., pull wire) can be used to facilitate navigating and bending of cholangioscope 324 through stomach 307, in addition to direct steering of cholangioscope 324 via the pull wires. For example, navigation of the Pyloric canal and Pyloric sphincter can be difficult to navigate using only an endoscope. Thus, the guide sheath 322 can be used to turn or bend elongate body of cholangioscope 324, or reduce the amount of steering or bending of the elongate body of the cholangioscope 324 required by pull wires, to facilitate traversing the Pyloric sphincter.

FIG. 3B is a schematic view of duodenum 308 connected to common bile duct 312 via duodenal papilla 314. Common bile duct 312 can branch off into pancreatic duct 316 and gallbladder duct 311. Duodenal papilla 314 can include sphincter of Oddi 310 that controls flow of bile and pancreatic juice into the intestine (duodenum). Pancreatic duct 316 can lead to pancreas 303. Pancreatic duct 316 carries pancreatic juice from pancreas 303 to the common bile duct 312. Gallbladder duct 311 can lead to gallbladder 305. In some patients, it can be difficult to navigate surgical instruments to duodenal papilla 314. It can also be difficult to navigate a surgical instrument into common bile duct 312 via insertion through duodenal papilla 314. Therefore, it is common during medical procedures to cut sphincter of Oddi 310 to enlarge duodenal papilla 314 to allow for easier access of instrument into common bile duct 312.

FIG. 4 is a diagram illustrating an example of mother-daughter endoscopes used in ERCP and a portion of patient anatomy of the procedure site. The mother-daughter endoscopes comprise an auxiliary scope 434 (cholangioscope) attached to and advanced through a lumen 432 of a main scope 400 (duodenoscope). The auxiliary scope 434 can comprise a lumen 436. The distal portion of the main scope 400 positioned in duodenum 308 comprises a functional module 402, an insertion section module 404, and a control module 406. The control module 406 can include, or be coupled to, a controller 408. Similar to the discussion above with respect to FIG. 1, the control module 406 can include other components, such as those described with reference to endoscopy system 10 (FIG. 1) and control unit 16 (FIG. 2). Additionally, the control module 406 can comprise components for controlling an imaging device (e.g., a camera) and a light source connected to the auxiliary scope 434, such as an imaging unit 410, a lighting unit 412 and a power unit 414. The main scope 400 can be configured similarly as endoscope 14 of FIGS. 1 and 2.

The functional module 402 of the main scope 400 can comprise an elevator portion 430. The auxiliary scope 434 can itself include functional components, such as camera lens 437 and a light lens (not illustrated) coupled to control module 406, to facilitate navigation of the auxiliary scope 434 from the main scope 400 through the anatomy and to facilitate viewing of components extending from lumen 432.

In ERCP, the auxiliary scope 434 can be guided into the sphincter of Oddi 310. Therefrom, a surgeon operating the auxiliary scope 434 can navigate the auxiliary scope 434 through the lumen 432 of the main scope toward the gallbladder 305, liver 304, or other locations in the gastrointestinal system to perform various procedures. In some examples, the auxiliary scope 434 can be used to guide an additional device to the anatomy to obtain biological matter (e.g., tissue), such as by passage through or attachment to lumen 436.

The biological sample matter can be removed from the patient, typically by removal of the additional device from the auxiliary device, so that the removed biological matter can be analyzed to diagnose one or more conditions of the patient. According to several examples, the mother-daughter endoscope assembly (including the main scope 400 and the auxiliary scope 434) can include additional device features, such as forceps or an auger, for gathering and removing cancerous or pre-cancerous matter (e.g., carcinoma, sarcoma, myeloma, leukemia, lymphoma and the like), or performing endometriosis evaluation, biliary ductal biopsies, and the like.

The controller 408 can include, or be coupled to, an endoscopic procedure data generator 450, and a treatment plan generator 460. The endoscopic procedure data generator 450 can generate images of an anatomical target, such as strictures or stenosis in biliary and pancreatic ductal system. In an example, the endoscopic procedure data generator 450 can generate real-time endoscope images of the anatomical target and its surrounding environment using an imaging sensor on the endoscope, such as a camera located at the functional section 30 of the endoscope 14. In some examples, the endoscopic procedure data generator 450 can receive images from external imaging devices such as X-ray or fluoroscopy images, electrical potential map or an electrical impedance map, CT scans, MRI scans such as obtained in MRCP, or acoustic images such as EUS images, among others. The endoscopic procedure data generator 450 may additionally generate or receive other procedure-related information, including sensor information (e.g., sensors associated with the endoscope or with a treatment device passing through the endoscope), device information, patient medical history etc. In some examples, the endoscopic procedure data generator 450 can retrieve, such as from a database, stored control log data (e.g., time-series data) of past endoscopic procedures performed by a plurality of physicians on a plurality of patients. The control log data can represent preferred cannulation and endoscope navigation approaches and habits of physicians with different experience levels.

The treatment plan generator 460, which is an example of the treatment generator 44 as illustrated in FIG. 2, can automatically generate a tissue acquisition plan based on images, alternatively or additionally on other information, produced by the endoscopic procedure data generator 450. The tissue acquisition plan can include identification of suitable tissue acquisition tools, methods of operating such tools and navigating the endoscope over which the tools are deployed, and an estimation of the amount of biopsy tissue collected using such tools, among other treatment or control parameters. According to some examples, the tissue acquisition plan can be generated or updated using a trained machine-learning (ML) model. The images of the anatomical target before, during, and after the biopsy procedure, and the tissue acquisition plan (represented in the form of texts or graphs) can be displayed to the operating physician. The tissue acquisition plan may additionally or alternatively be used to facilitate operation of the tissue acquisition tool or an endoscope in a robot-assisted biopsy procedure.

Figure 5C:
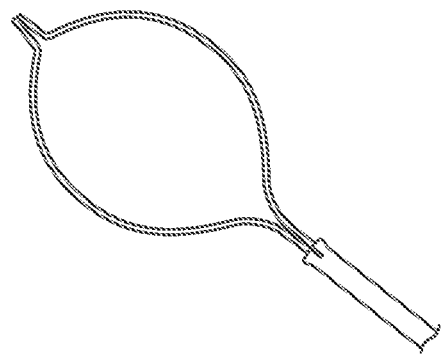
FIG. 5A-5C are diagrams illustrating examples of tissue acquisition tools used in ERCP biopsy procedures.
Figure 5B:
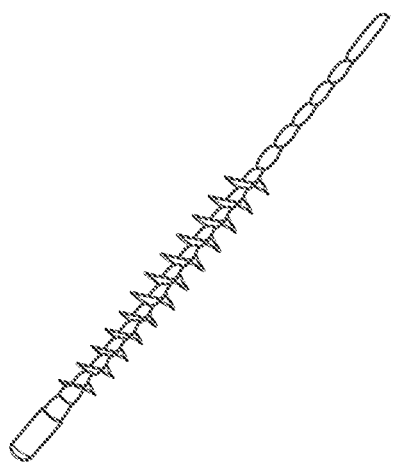
Figure 5A:
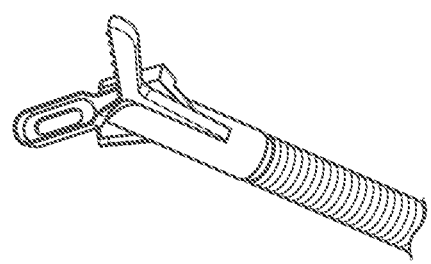

Various tissue acquisition tools have been used in endoscopic biopsy procedures to collect tissue samples. FIGS. 5A-5C illustrate, by way of example and not limitation, tissue acquisition tools to choose from in an ERCP biopsy procedure. FIG. 5A illustrates endoscopic biopsy forceps that can enter the gastrointestinal tract via a flexible endoscope to perform biopsy at the anatomical target. The forceps may come with different size to fit into a particular endoscope channel. The forceps may include a cup to facilitate capturing and collecting the biopsied tissue. The cup can be an oval cup, or alligator cup with serrated jaws to prevent slippage. A blade inside the cup can deliver sharp cutting performance to ensure clean-edged specimens. Some forceps include a swinging jaw mechanism to aid tangential biopsies. Some forceps include a needle for improved anchorage.

FIG. 5B illustrates an endoscopic biopsy brush including bristles to brush off and collect biopsy tissue. The brush can be delivered via a flexible endoscope to perform biopsy at the anatomical target. Like the biopsy forceps, the biopsy brushes may come with different size to fit into a particular endoscope channel and for easy insertion. The brush may be built on a control wire that provides increased warp resistance, improved insertion ability, and easier brushing capabilities. Some biopsy brushes include stiffer bristles and soft bristles in one brush. The stiffer bristles are to assist in creating a defect in the target tissue, and the softer bristles are to capture specimens after tissue debridement.

FIG. 5C illustrates a biopsy snare that can enter the gastrointestinal tract via a flexible endoscope and reach an anatomical target, grasp, dissect, and transect tissue therein. The snare may include one or more loops of particular shapes, e.g., circle, oval, hexagon, or diamond shaped loops. In ERCP, after placing the tip of the duodenoscope on an anatomical target, a snare can be deployed from the endoscope, opens up so that it can encircle the base of the target. Constant tension was applied to the snare loop during excision until the lesion was transected. Some snares have loops made of braided wire (such snares are therefore named "braided snares") to prevent or reduce slippage and improve gripping force, thereby enhancing the precision in tissue transection.

Figure 6:
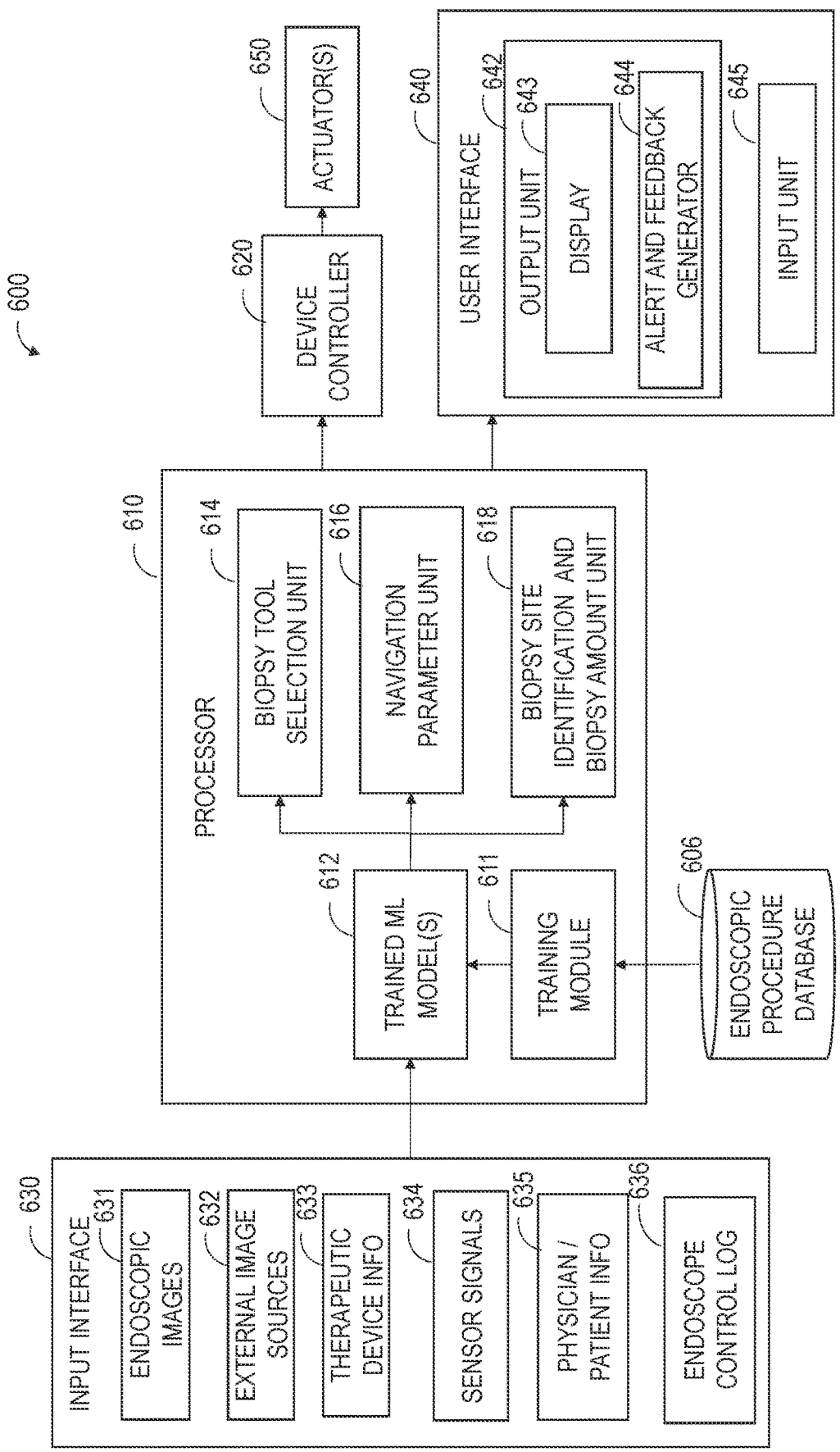
FIG. 6 is a block diagram illustrating an example of an endoscopic procedure planning system to automatically generate a tissue acquisition plan for use in an endoscopic tissue acquisition procedure such as biopsy.

FIG. 6 is a block diagram illustrating an example of an endoscopic procedure planning system 600 to automatically generate a tissue acquisition plan for use in an endoscopic tissue acquisition procedure such as biopsy. The tissue acquisition plan may include a recommended tissue acquisition tool and proper manipulation of such tool to acquire an adequate amount of biopsy tissue. The system 600 can be a part of the control unit 16 in FIG. 1, or the controller 408 in FIG. 4 along with other devices or functional units such as the endoscopic procedure data generator 450 and the treatment plan generator 460. The system 600 can include a processor 610, a device controller 620, an input interface 630, and a user interface device 640. In some examples, the system 600 can include or be communicatively coupled to an endoscopic procedure database 606.

The processor 610 may include circuit sets comprising one or more other circuits or sub-circuits that may, alone or in combination, perform the functions, methods, or techniques described herein. In an example, the processor 610 and the circuits sets therein may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The processor 610 may generate a tissue acquisition plan using various sources of data specific to a patient received from the input interface 630. In some embodiments, the input interface 630 may be a direct data link between the system 600 and one or more medical devices that generate at least some of the input features. For example, the input interface 630 may transmit endoscopic images 631, external image sources 632, or sensor signals 634 directly to the system 600 during a therapeutic and/or diagnostic medical procedure. Additionally or alternatively, the input interface 630 may be a classical user interface that facilitates interaction between a user and the system 600. For example, the input interface 630 may facilitate a user interface through which the user may manually enter some input data to the system 600. Additionally or alternatively, the input interface 630 may provide the system 600 with access to an electronic patient record from which one or more data features may be extracted. In any of these cases, the input interface 630 can collect one or more of the following sources of data in association with a specific patient on or before a time at which the system 600 is used to identify an anatomical target and generate a tissue acquisition plan to collect biopsied tissue from the anatomical target.

By way of example and not limitation, data received from the input interface 630 may include one or more of endoscopic images 631 of the anatomical target, external image sources 632, endo-therapeutic device information 633, sensor signals 634, or physician/patient information 635, as illustrated in FIG. 6. The endoscopic images 631 may include real-time endoscope images of the anatomical target and its surrounding environment (e.g., biliary duct strictures) captured by an imaging sensor associated with the endoscope during an endoscopic procedure, such as DPOC or ERCP as described above. The external image sources 632 may include pre- or peri-procedural images of the anatomical target acquired by external imaging devices other than the endoscope, which may include, for example, X-ray or fluoroscopy images, electrical potential map or an electrical impedance map, CT images, MRI images such as images obtained during MRCP, or acoustic images such as EUS images, among others. The endo-therapeutic device information 633 may include specification data, including size, dimension, shape, and structures of the endoscope used in an ERCP procedure or other steerable instruments such as a cannular, a catheter, or a guidewire; size, dimension, shape, and structures of tissue acquisition tools (e.g., knives, forceps, brushes, snares, suction devices). Such device specification information may be used to determine cannulation or navigation parameter values such as the angle and/or the force applied to the device, or for selecting suitable tools and determining tool operational parameters to effectively and efficiently acquire a sufficient amount of biopsy tissue. The sensor signals 634 may be acquired by sensors coupled to the endoscope or a treatment device passing through the endoscope, or otherwise associated with the patient. In an example, the sensor signals 634 may be acquired by a proximity sensor at a distal portion of the endoscope. Examples of the sensor signals 634 may include position, direction, or proximity of a distal portion of the endoscope relative to an anatomical target. The physician/patient information 635 may include the operating physician's habits or preference of using a steerable elongate instrument, such as a preferred approach for cannulation and endoscope navigation, or past procedures of the similar type to the present procedure performed by the physician and the corresponding procedure outcome (e.g., success/failure assessment, procedure time, prognosis and complications). The physician/patient information 635 may include patient information, including patient demographics (e.g., age, gender, race), patient medical history such as prior endoscopic procedures and images or data associated therewith, etc. The endoscope control log data 636 may include time-series data representing changes in the movement and deflection of the device (e.g., endoscope, catheter, or cannula) on the endoscopic image as being maneuvered during a procedure.

The processor 610 may include one or more of a biopsy tool selection unit 614, a navigation parameter unit 616, and a biopsy site identification and biopsy amount unit 618. The biopsy tool selection unit 614 can automatically determine a biopsy tool recommendation for use in endoscopic biopsy based on an input image (e.g., endoscopic images 631 and/or external image sources 632). Other data from the input interface 630 may additionally or alternatively be used to determine the biopsy tool recommendation, such as size and geometry of candidate tools (as a part of the endo-therapeutic device information 633), sensor data indicating spatial restrictions of an environment of the anatomical target (as a part of the sensor signals 634), or size, location, morphology, among other characteristics of the anatomical target as estimated by the biopsy site identification and biopsy amount unit 618, as discussed further below. In an example, the biopsy tool recommendation can be selected from brushes, forceps, knives, snares, or suction devices. In some examples, the biopsy tool selection unit 614 can recommend a tool size for a particular biopsy tool.

The biopsy tool selection unit 614 can automatically determine tool operation, such as recommended values of one or more operational parameters for navigating and manipulating the tool during the procedure to safely and more effectively collect a sufficient amount of biopsy tissue. Similar to the tool recommendation above, the biopsy tool selection unit 614 can determine values of the tool operational parameters using input image such as endoscopic images 631 and/or external image sources 632, other information from the input interface 630, or characteristics of the biopsy site as identified by the biopsy site identification and biopsy amount unit 618. The tool operational parameters can vary depending on the type of the tool used for tissue acquisition. For example, for endoscopic forceps, the tool operational parameters can include forceps location; orientation, angle, or orbit of the forceps towards the biopsy site; advance length or distance from the biopsy site; jaw opening states such as having one jaw open or both jaw open (as illustrated in FIG. 5A), among others. Propper operational parameters as determined by the biopsy tool selection unit 614 can assist the operating physician in precisely collecting a desired amount of tissue while minimizing complication and preserving functionality of the anatomy at the biopsy site.

The navigation parameter unit 616 can automatically estimate navigation parameters of an endoscope (or other steerable elongate instrument) over which the tissue acquisition device is deployed. Examples of the navigation parameters can include: distance from the endoscope distal portion to duodenal papilla; a heading direction of the distal portion of the endoscope relative to the biopsy site; an insertion angle of a cannula or a surgical element used in cannulation; a protrusion amount of a cannula or a surgical element; a speed or a force applied to the endoscope distal portion or a surgical element: a rotational direction or a cutting area of a surgical element; among others. In some examples, the navigation parameter unit 616 can estimate a probability of success, or estimated procedure time, associated with the use of the selected biopsy tool in accordance with the automatically determined tool operational parameters and the estimated endoscope navigation parameters.

The biopsy site identification and biopsy amount unit 618 can use an input image (e.g., endoscopic images 631 and/or external image sources 632), or image features extracted from the input image, to automatically identify a biopsy site and determine one or more characteristics thereof. Examples of the biopsy site characteristics can include location, size, and shape of the tissue at the biopsy site. In some examples, the biopsy site identification and biopsy amount unit 618 can recognize pathophysiological properties of the tissue at the biopsy site, such as an inflammation state, a stricture level, or a malignancy state (e.g., degree or area of invasion by cancer) of the tissue to be acquired. The biopsy site identification and biopsy amount unit 618 can estimate an amount of biopsy tissue to be collected using the recommended biopsy tool. The estimate of the amount of biopsy tissue can be based an image of the biopsy site, type of the acquisition tools and the tool operational parameters, among other information received at the input interface 630.

One or more of the biopsy tool selection unit 614, the navigation parameter unit 616, or the biopsy site identification and biopsy amount unit 618 can each use one or more trained machine-learning (ML) models 612 to perform their respective tasks as stated above. The ML model(s) can have a neural network structure comprising an input layer, one or more hidden layers, and an output layer. The input interface 630 may deliver one or more sources of input data, or features generated therefrom, into the input layer of the ML model(s) 612 which propagates the input data or data features through one or more hidden layers to the output layer. The ML model(s) 612 can provide the system 600 with the ability to perform tasks, without explicitly being programmed, by making inferences based on patterns found in the analysis of data. The ML model(s) 612 explores the study and construction of algorithms (e.g., ML algorithms) that may learn from existing data and make predictions about new data. Such algorithms operate by building the ML model(s) 612 from training data in order to make data-driven predictions or decisions expressed as outputs or assessments.

The ML model(s) 612 may be trained using supervised learning or unsupervised learning. Supervised learning uses prior knowledge (e.g., examples that correlate inputs to outputs or outcomes) to learn the relationships between the inputs and the outputs. The goal of supervised learning is to learn a function that, given some training data, best approximates the relationship between the training inputs and outputs so that the ML model can implement the same relationships when given inputs to generate the corresponding outputs. Unsupervised learning is the training of an ML algorithm using information that is neither classified nor labeled, and allowing the algorithm to act on that information without guidance. Unsupervised learning is useful in exploratory analysis because it can automatically identify structure in data.

Common tasks for supervised learning are classification problems and regression problems. Classification problems, also referred to as categorization problems, aim at classifying items into one of several category values. Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM). Examples of DNN include a convolutional neural network (CNN), a recurrent neural network (RNN), a deep belief network (DBN), or a hybrid neural network comprising two or more neural network models of different types or different model configurations.

Some common tasks for unsupervised learning include clustering, representation learning, and density estimation. Some examples of commonly used unsupervised learning algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

As illustrated in FIG. 6, the ML model(s) 612 may be trained using a training module 611, which can be included in the processor 610 as shown in FIG. 6. Alternatively, the training module 611 can be implemented in a separate unit. To train an ML model, a training dataset can be constructed using past endoscopic procedure data such as selected and retrieved from the endoscopic procedure database 606. The training data may include procedure data acquired during respective endoscopic procedures performed on a plurality of patients. The endoscopic procedures can be those of the same type as the endoscopic procedure to be performed on the present patient. The training data can be from various data sources, such as any of those shown in the input interface 630. The training data used for training an ML model can vary depending on the parameters to estimate. In an example of a ML-based determination of canulation and endoscope navigation, the training data can include endoscopic images or videos showing patient anatomy, cannulation and endoscope navigation routes, progress of cannulation or navigation, among other information. In an example of a ML-based biopsy tool selection for use in an endoscopic tissue acquisition procedure, the training data can include past endoscopic images or images from external sources showing the biopsy sites, and information of tools used in past procedures at respective biopsy sites. The tool information can include type, size, operational data associated with the use of such tools in past procedures (which can be recorded during the procedure, or obtained offline via analysis of the endoscopic images or videos), and procedure outcome (e.g., success/failure assessment of the procedure, total procedure time, procedure difficulty and skills requirement, etc.)

In an example, the training data can be screened such that only data of procedures performed by certain physicians (such as those with substantially similar experience levels to the operating physician), and/or data of procedures on certain patients with special requirement (such as those with substantially similar anatomy or patient medical information to the present patient) are included in the training dataset. In an example, the training data can be screened based on a success rate of the procedure, including times of attempts before a successful cannulation or navigation, such that only data of procedures with a desirable success rate achieved within a specified number of attempts are included in the training dataset. In another example, the training data can be screened based on complication associated with the patients. In some examples, particularly in case of a small training dataset (such as due to data screening), the ML model can be trained to identify a suitable tissue acquisition tool and methods of operating such tool at the biopsy site, determine navigation parameters of the endoscope for delivering the tissue acquisition tool, and identify characteristics of the biopsy site and estimate an amount of biopsied tissue by extrapolating, interpolating, or bootstrapping the training data, thereby creating a tissue acquisition plan specifically tailored to the specific patient and physician. The training of the ML model may be performed continuously or periodically, or in near real time as additional procedure data are made available. The training involves algorithmically adjusting one or more ML model parameters, until the ML model being trained satisfies a specified training convergence criterion.

In some examples, a plurality of ML models can be separately trained, validated, and used (in an inference phase) in different applications, such as estimating different parameters of the devices used in an endoscopic procedure or planning of such a procedure. For example, a first ML model (or a first set of ML models) may be trained to establish a correspondence between (i) endoscopic images and/or other external images of biopsy sites from past endoscopic procedures (optionally along with other information) and (ii) tissue acquisition tools used in those past procedures, and the tool characteristics including their types, sizes, and operational parameters. The trained first ML model(s) can be used by the biopsy tool selection unit 614 in an inference phase to automatically determine, from an input image (or a sequence of images or a live video) of an anatomical target (optionally along with other information), a tissue acquisition tool recommendation including a recommend tool of a particular type and size and operational parameters for manipulating to tool to collect tissue from the anatomical target.

In an example, a second ML model (or a second set of ML models) may be trained to establish a correspondence between (i) endoscopic images and/or other external images of biopsy sites from past endoscopic procedures (optionally along with other information) and (ii) navigation and treatment parameters in those past procedures, including direction, angle, speed, force, and amount of intrusion for navigating and placing endoscopes, catheters, or other steerable elongate instrument over which a tissue acquisition device is deployed, or estimated success rate and procedure time, among other parameters. The trained second ML model(s) can be used by the navigation parameter unit 616 in an inference phase to automatically determine, from an input image (or a sequence of images or a live video) of patient anatomy including the anatomical target (optionally along with other information), proper navigation parameters that may be used as a procedure guidance.

In an example, a third ML model (or a third set of ML models) may be trained to establish a correspondence between (i) endoscopic images and/or other external images of biopsy sites from past endoscopic procedures (optionally along with other information) and (ii) characteristics of the biopsy site such as location, size, shape, orientation, and pathophysiological properties of the tissue at the biopsy site such as an inflammation state, or a malignancy state of the tissue to be acquired. The trained third ML model(s) can be used by the biopsy site identification unit and the biopsy amount unit 614 in an inference phase to identify, from an input image (or a sequence of images or a live video) of an anatomical target (optionally along with other information), characteristics of the biopsy site.

In an example, a fourth ML model (or a fourth set of ML models) may be trained to establish a correspondence between (i) biopsy images from past procedures illustrating anatomy of the biopsy sites and operations of tissue acquisition tools towards the biopsy sites during past endoscopic procedures (optionally along with other information) and (ii) an amount of biopsied tissue acquired from those previous procedures. The trained fourth ML model(s) can be used by the biopsy site identification and biopsy amount unit 618 in an inference phase to estimate, from an input biopsy image (or a sequence of images or a live video) during an endoscopic biopsy procedure (optionally along with other information) illustrating the biopsy site and the tissue acquisition tool relative to the biopsy site, an amount of biopsy tissue that can be collected using the tissue acquisition tool.

The device controller 620 can generate a control signal to one or more actuators 650, such as a motor actuating a robot arm. The one or more actuators 650 can be coupled to a steerable elongate instrument, which can be a diagnostic or therapeutic endoscope, a cannula, a catheter, a guidewire, or a guide sheath, among others. The steerable elongate instrument may include a treatment tool (e.g., a lithotripsy device or a calculi extraction device) robotically operable via the one or more actuators 650. In response to the control signal, the one or more actuators 650 can robotically adjust position, posture, direction, and navigation path of the steerable elongate instrument and a tissue acquisition tool included therein in accordance with the navigation parameters estimated by the navigation parameter unit 616, and/or the tool operational parameters estimated by the biopsy tool selection unit 614.

As some of the canulation or navigation parameters (e.g., positions, angle, direction, navigation path) associated with a cannula or GW are determined based on images (e.g., endoscopic images or other images) generated an imaging system, such canulation or navigation parameters are with reference to the coordinates of the imaging system. To facilitate robotic control of the cannula or GW in accordance with the canulation or navigation parameters, in some examples the coordinates of the robotic system may be registered with the coordinates of the imaging system, such that an anatomical position in the coordinates of the imaging system can be mapped to a corresponding position in the coordinates of the robotic system. Such registration may be performed, for example, by using distinct landmarks whose positions are known in respective coordinate systems. The registration may be intensity- or feature-based, and can be represented by transformation model (a linear or a non-linear model) that maps the coordinates of imaging system to the coordinates of the robotic system.

The user interface device 640 can include an output unit 642 and an input unit 645, which are examples of the output unit 18 and the input unit 20 respectively as shown in FIG. 2. The input unit 645 can receive input from the user or from other data sources. In an example, the input interface 630 can be included in the input unit 645. The output unit 642 can include a display 643 that can display images of the biopsy site and various characteristics thereof as identified by the biopsy site identification and biopsy amount unit 618, tool recommendations including information about the type and size of the tools, and recommended methods of operating such tools such as values of one or more operational parameters generated by the biopsy tool selection unit 614. In some examples, the display 643 can present a graphical representation of the navigation of an endoscope based on the navigation parameters produced by the navigation parameter unit 616, and/or a graphical representation of the operation of a biopsy tool based on the tool operational parameters produced by the biopsy tool selection unit 614.

In an example, the displayed region of the anatomical target images can be automatically adjusted according to the position or direction of a distal end of the endoscope relative to an anatomical target. For example, the output unit 642 may automatically zoom in an image as the endoscope tip gets closer to the papilla to show more details of the papilla. Alternatively, the zooming function can be activated and adjusted manually by the user (e.g., operating physician) via the input unit 645. In an example, the output unit 642 can display a cross-section view of an anatomy in a direction specified by a user, such as via the input unit 645. In an example, the user may adjust viewing angle (e.g., rotating the view) and have a 360-degree view of the reconstructed or integrated 3D images via the input unit 645. In an example, at least a portion of the input unit 645 can be incorporated into the endoscope, such as the handle section 32 of endoscope 14, to facilitate user operation during the procedure.

In some examples, the display 643 may automatically center the anatomical target in a viewing area, such as based on the distance and viewing angle of the imaging device (e.g., camera) relative to the anatomical target. In an example, the processor 610 can control the positioning and direction of the endoscope to adjust viewing angle of the imaging device to achieve auto-centering of the anatomical target. Additionally or alternatively, the processor 610 can post-process the acquired image including re-positioning the identified anatomical target at the center of the viewing area.

In some examples, the output unit 642 may display on the image a visual indication of the anatomical target (e.g., duodenal papilla), a projected navigation path toward the anatomical target; or a progression of the endoscope toward the targe anatomy along the projected navigation path. Display settings can be adjusted by the user via the input unit 645. The visual indication may take the format of markers, annotations (icons, texts, or graphs), highlights, or animation, among other visual indicators. For example, markers of different shapes, colors, forms, or sizes can be display on the reconstructed or integrated image to distinguish different tissue, anatomical regions, their accessibility or criticality.

In some examples, the output unit 642 can generate supportive data for the tissue acquisition sites such as recognized by the biopsy site identification and biopsy amount unit 618. Such supportive data can take the format of a list, a lookup table, or printed labels for the tissue acquisition sites. The supportive data can help avoid mislabeling of tissue samples biopsied from different sites. In an example, the processor 610 can register one or more biopsy sites that are either automatically recognized or manually identified by a user via the input unit 645. Following an endoscopic biopsy procedure at the one or more registered biopsy sites, the biopsy tissue samples can be identified by their respective biopsy sites, and a list or labels can be created and provided to the user.

The output unit 642 can include an alert and feedback generator 644 that can generate an alert, a notification, or other formats of human-perceptible feedback to the operating physician on the status or progress of the cannulation or navigation in reference to the navigation plan. For example, an alert can be generated to indicate a risk of tissue damage associated with improper cannulation. The feedback can be in one or more forms of audio feedback, visual feedback, or haptic feedback. For example, when the endoscope tip enters or comes closer to a "critical zone" (e.g., proximity sensor detecting a distance to a critical anatomy of interest shorter than a threshold distance), the critical zone can be shown in different colors to represent such distance (e.g., green zone, yellow zone, and read zone as the endoscope gets closer to the critical zone). Additionally or alternatively, haptic feedback such as touch or vibration may be generated and felt by the operating physician. In an example, the alert and feedback generator 644 can automatically adjust the vibration strength according to the distance to the critical zone. For example, a low vibration can be generated when the endoscope tip is in a green zone. If the system predicts, based on present advancing speed and direction of the endoscope, that the endoscope tip will reach the critical zone in a time lower than a predetermined threshold, then alert and feedback generator 644 can apply moderate vibration when the endoscope tip reaches a yellow zone, and apply high vibration when the endoscope tip reaches red zones to indicate a risk of tissue damage. The real-time alert and feedback in an image-guided endoscopic procedure as described herein can improve the efficiency of cannulation and endoscope navigation, especially for inexperienced physicians, and can improve endoscopic procedure success rate and patient outcome.

Following the tissue acquisition procedure in accordance with the tissue acquisition plan (e.g., using the automatically determined acquisition tool and operational and navigation parameters), the processor 610 can assess adequacy of the amount of tissue collected, such as based on a comparison of the images of the biopsy site before and after the tissue acquisition. If the comparison reveals that the area of the biopsy site is reduced by an amount less than a threshold, then the biopsied tissue amount is deemed inadequate. An alert can be generated, and additional biopsy can be recommended to the user.

Figure 7A:
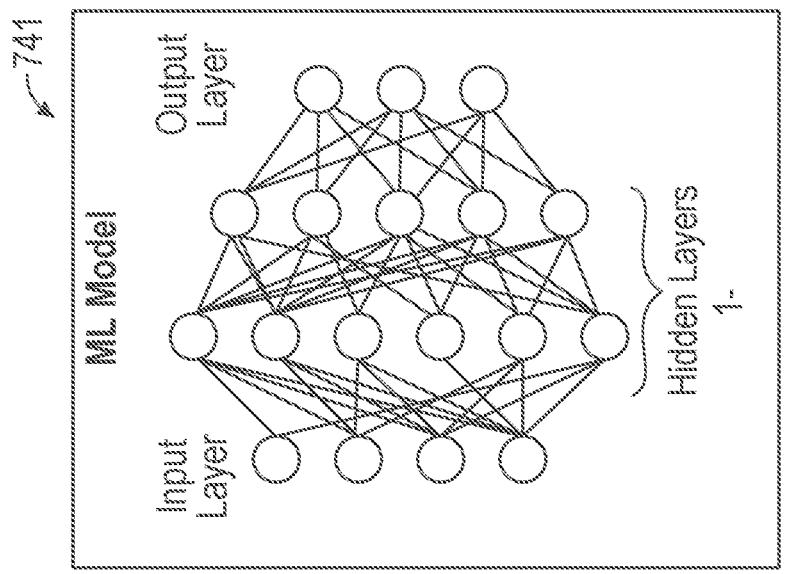
FIGS. 7A-7D are diagrams illustrating examples of training an ML model and using the trained ML model to generate a tissue acquisition plan for endoscopically collecting tissue from a biliary ductal stricture.
Figure 7A:
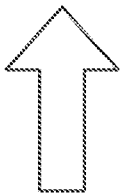
Figure 7A:
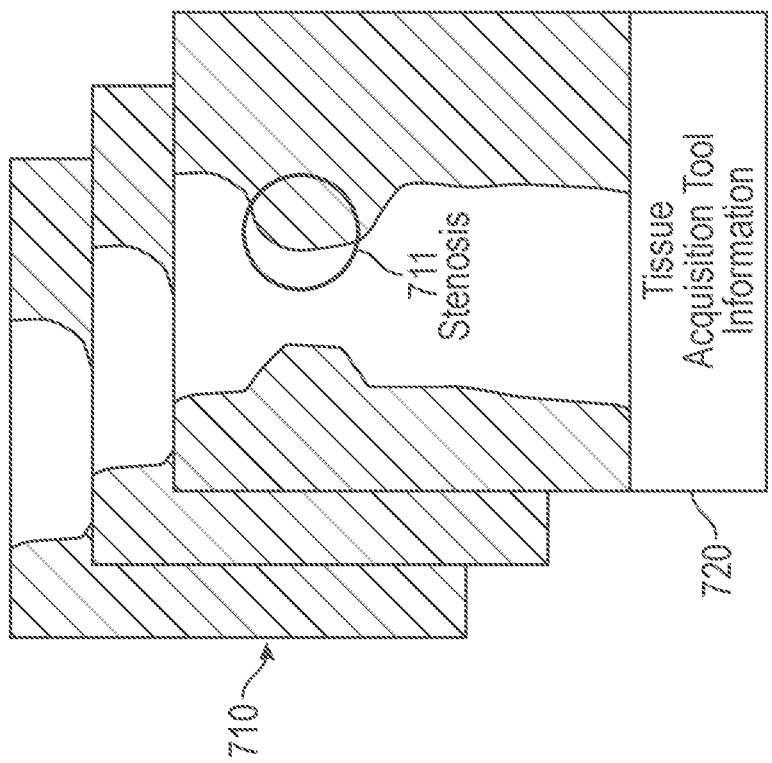

FIGS. 7A-7D are diagrams illustrating examples of training an ML model and using the trained ML model to generate a tissue acquisition plan for endoscopically collecting tissue from a biliary ductal stricture. FIG. 7A illustrates an ML model training (or learning) phase during which an ML model 741 may be trained using training data comprising a plurality of images 710 of respective biliary ductal strictures 711 from past endoscopic tissue acquisition procedures performed on a plurality of patients. The training data may also include annotated procedure data 720 including information about the tissue acquisition tools used in each of the procedures, such as biopsy forceps of particular size and characteristics. The tool information can include type, size, operational data associated with the use of such tools in the past endoscopic tissue acquisition procedures. The training data may also include procedure outcome, such as success/failure assessment of the procedure, total procedure time, procedure difficulty and skills requirement, etc. The ML model 741 can be trained using supervised learning, unsupervised learning, or reinforcement leaning. Examples of ML model architectures and algorithms may include, for example, decision trees, neural networks, support vector machines, or a deep-learning networks, etc. Examples of deep-learning networks include a convolutional neural network (CNN), a recurrent neural network (RNN), a deep belief network (DBN), or a hybrid neural network comprising two or more neural network models of different types or different model configurations.

The training of the ML model may be performed continuously or periodically, or in near real time as additional procedure data are made available. The training process involves algorithmically adjusting one or more ML model parameters, until the ML model being trained satisfies a specified training convergence criterion. The trained ML model 741 can establish a correspondence between the images of the biliary ductal strictures from past endoscopic procedures and the tissue acquisition tools and the tool operational parameters.

Figure 7B:
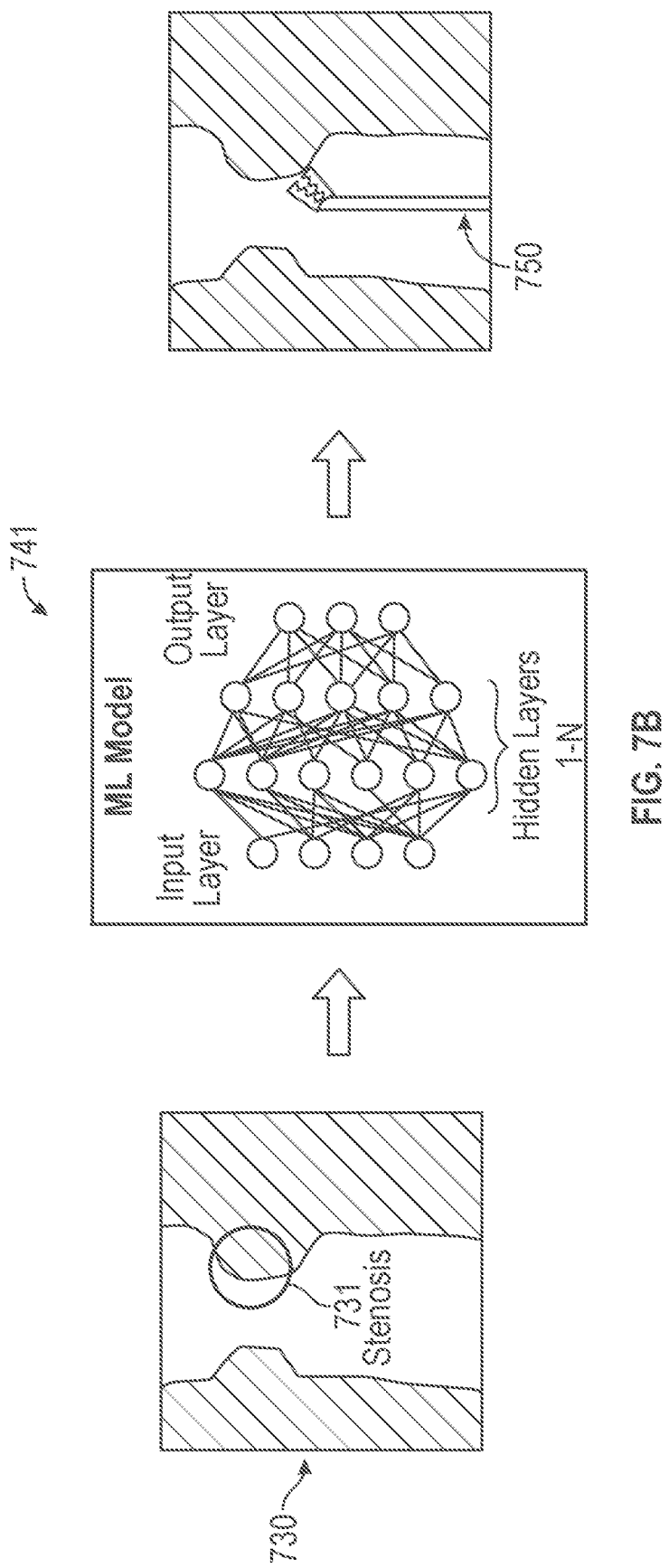

FIG. 7B illustrates an inference phase during which a live image 730 of a biliary ductal stricture 731 is applied to the trained ML model 741 to automatically determine a tissue acquisition tool recommendation 750 (which is biopsy forceps with serrated jaws in this example). The tool recommendation can be communicated to a user (e.g., a physician) to assist in procedure planning. Additionally or alternatively, the tool recommendation may be provided to a robotic system to facilitate a robot-assisted tissue acquisition procedure.

Figure 7C:
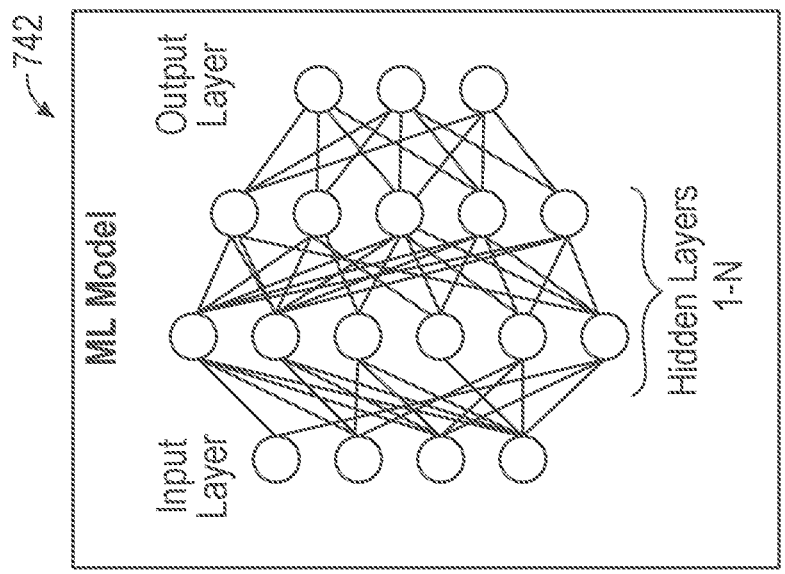
Figure 7C:
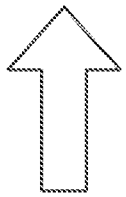
Figure 7C:
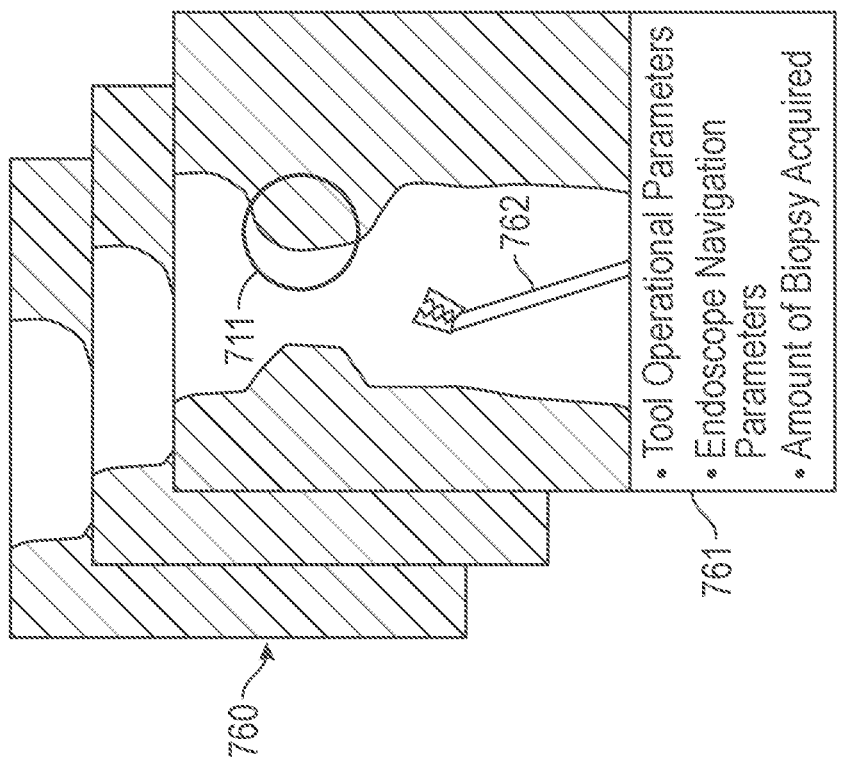

FIG. 7C illustrates an ML model training (or learning) phase during which an ML model 742 may be trained to estimate operational parameters for a tissue acquisition tool (such as the recommended tool as determined by the trained ML model 741). In some examples, the ML model 742 may also be trained to estimate navigation parameters of an endoscope (or another steerable elongate instrument) for delivering the tissue acquisition tool. The training data may comprise a plurality of biopsy images 760 from past endoscopic biopsy procedures representing anatomy of the biliary ductal stricture 711. The training data may also include information of tissue acquisition tool 762 used each of the past procedures corresponding to the plurality of images 760, and information of the endoscope navigation and tool operational parameters 761. In some examples, the training data may include amount of biopsy tissue collected from the previous procedures corresponding to the biopsy images. The training data may also include procedure outcome, such as success/failure assessment of the procedure, total procedure time, procedure difficulty and skills requirement, etc. Similar to the ML model 741 above, the ML model 742 can have a particular architecture, and can be trained using supervised learning, unsupervised learning, or reinforcement leaning.

The trained ML model 742 can establish a correspondence between the biopsy images from past endoscopic procedures and endoscope navigation and tool operational parameters. In some examples, the trained ML model 742 can further establish a correspondence between the biopsy images from past endoscopic procedures and the amount of biopsied tissue acquired from those previous procedures.

Figure 7D:
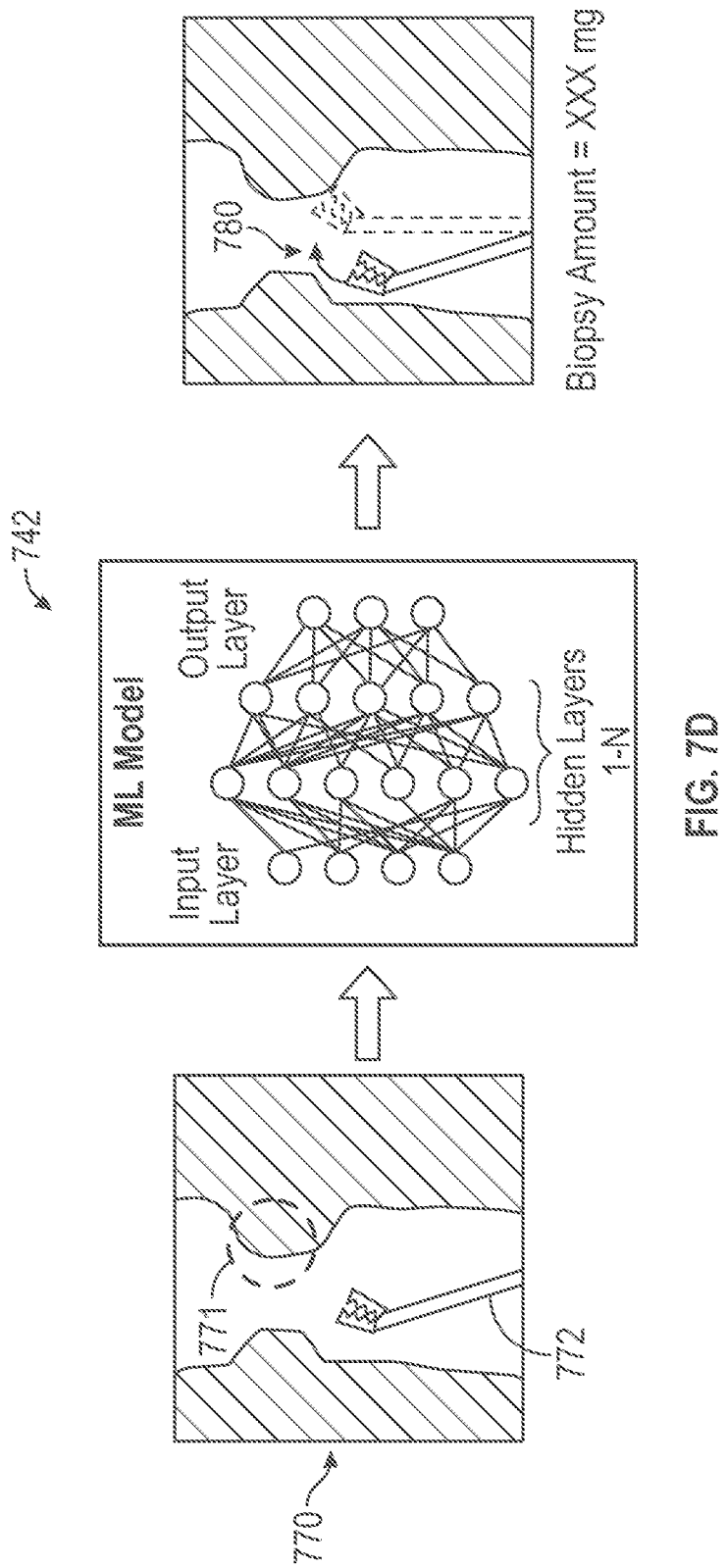

FIG. 7D illustrates an inference phase during which a live biopsy image 770 of a biliary ductal stricture 771 is applied to the trained ML model 742 to determine operational parameters for maneuvering the tissue acquisition tool 772 and endoscope navigation parameters. The determined tool operational parameters and the endoscope navigation parameters can be communicated to a user (e.g., a physician) to assist in procedure planning. In the example as illustrated in FIG. 7D, the automatically determined tool operational parameters can be represented by a graph 780 showing desired location, posture, orientation, and an advancement path of the tissue acquisition tool 772 relative to the biopsy site of the stricture 771. In some examples, the estimated operational parameters for maneuvering the tissue acquisition tool 772 may be used to facilitate robotic maneuvering of the tissue acquisition tool in a robot-assisted procedure. In some examples, the inference may additionally include an estimate of the amount of the biopsied tissue that can be acquired from the biliary ductal stricture 771 using the tissue acquisition tool 772 according to the automatically determined tool operational parameters.

Figure 8:
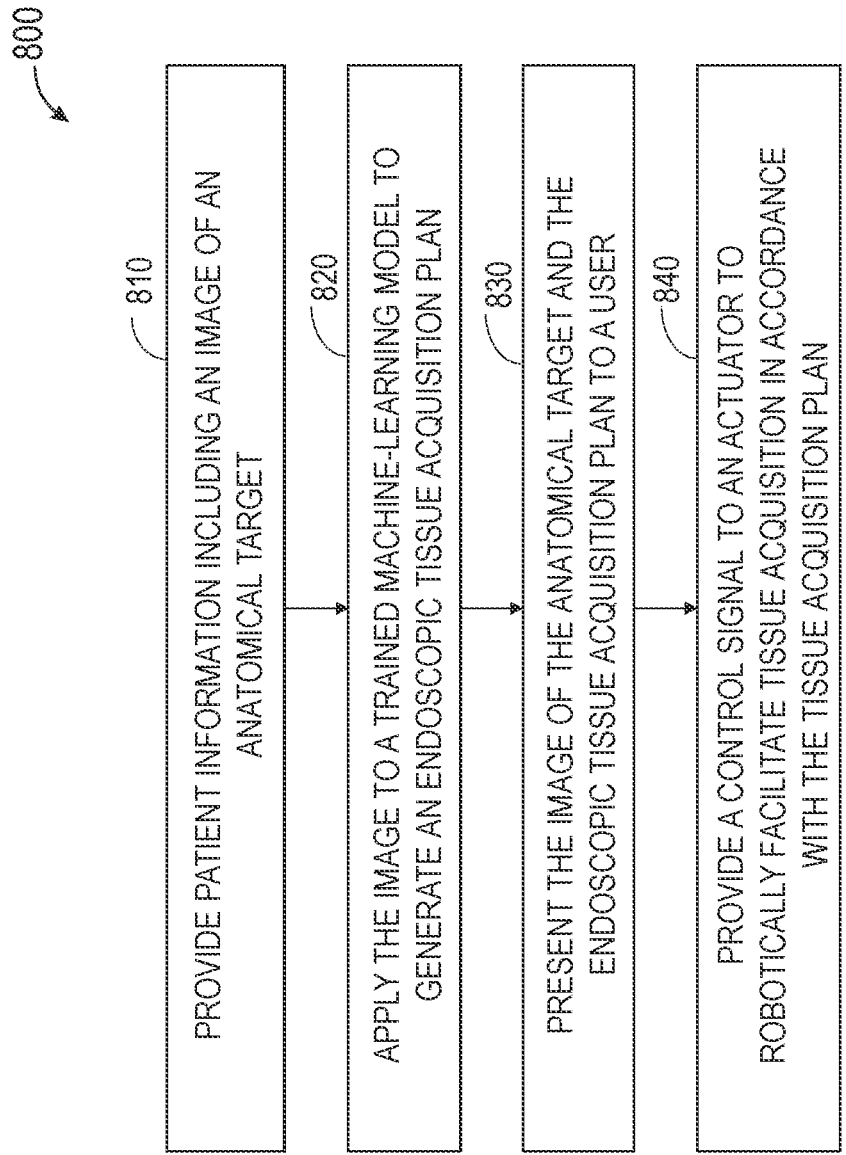
FIG. 8 is a flow chart illustrating an example method for planning an endoscopic tissue acquisition procedure via a endoscopic system.

FIG. 8 is a flow chart illustrating an example method 800 for planning an endoscopic tissue acquisition procedure via a endoscopic system, such as the endoscopic procedure planning system 600 as illustrated in FIG. 6. The method 800 may be used to acquire an adequate amount of biopsy tissue in an endoscopic biopsy procedure. Although the processes of the method 800 are drawn in one flow chart, they are not required to be performed in a particular order. In various examples, some of the processes can be performed in a different order than that illustrated herein.

At 810, patient information including an image of an anatomical target can be provided for use in automatic planning of an endoscopic tissue acquisition procedure. The image of the anatomical target may include real-time endoscope images of the anatomical target and its surrounding environment captured by an imaging sensor associated with the endoscope during an endoscopic procedure, such as DPOC or ERCP, or images from other sources including, for example, X-ray or fluoroscopy images, electrical potential map or an electrical impedance map, CT images, MRI images such as images obtained from Magnetic resonance cholangiopancreatography (MRCP) procedures, or acoustic images such as endoscopic ultrasonography (EUS) images, among others. In addition to the images of the anatomical target, other information may be used in the procedure planning process, including, for example, endo-therapeutic device information, sensor signals, physician information (e.g., the operating physician's habits or preference of using the steerable elongate instrument), and endoscope control log data, as described above with reference to FIG. 6.

At 820, the images of the anatomical target, and optionally other information received at step 810, may be provided to a trained machine-learning (ML) model to generate an endoscopic tissue acquisition plan for acquiring tissue from the anatomical target. The ML model may be trained using procedure data from past endoscopic procedures on a plurality of patients. The past procedure data can include images of anatomical targets of the plurality of patient and assessments of tissue acquisition plans corresponding to the images of anatomical targets. The trained ML model may be used to automatically determine a recommended biopsy tool of a specific type or size for use in for use in endoscopic biopsy based at least on the input image. Other data may additionally or alternatively be used to make such tool recommendation, including, for example, position of the anatomical target, spatial restrictions of an environment of the anatomical target, or sizes or geometries of candidate biopsy tools. Examples of the recommended biopsy tool can include a brush, forceps, a knife, a snare, or a suction device.

The same trained ML model, or a separately trained ML model may automatically determine proper tool operations, such as recommended values of one or more operational parameters for navigating and manipulating the tool during the procedure to safely and more effectively collect a sufficient amount of biopsy tissue, based at least on the input image. The tool operational parameters can vary depending on the type of the tool used for tissue acquisition. For example, for endoscopic forceps, the tool operational parameters can include forceps location; orientation, angle, or orbit of the forceps towards the biopsy site, advance length or distance from the biopsy site; jaw opening states such as having one jaw open or both jaw open, among others.

The same trained ML model, or a separately trained ML model may automatically estimate navigation parameters of an endoscope (or other steerable elongate instrument) over which the tissue acquisition device is deployed, such as a distance from the endoscope distal portion to duodenal papilla; a heading direction of the distal portion of the endoscope relative to the biopsy site; an insertion angle of a cannula or a surgical element used in cannulation; a protrusion amount of a cannula or a surgical element; a speed or a force applied to the endoscope distal portion or a surgical element; a rotational direction or a cutting area of a surgical element; among others. In some examples, the trained ML model may be used to determine a probability of success, or an estimate of treatment time in accordance with the tissue acquisition plan (including the recommended biopsy tool, the automatically determined tool operational parameters, and the estimated endoscope navigation parameters).

The same trained ML model, or a separately trained ML model may automatically identify a biopsy site and determine one or more characteristics thereof. The characteristics of the biopsy site can include location, size, shape of the tissue at the biopsy site. In some examples, the characteristics of the biopsy site can include pathophysiological properties such as an inflammation state, a stricture level, or a malignancy state (e.g., degree or area of invasion by cancer) of the tissue at the biopsy site. The trained ML model may additionally estimate an amount of biopsy tissue that can be collected using the recommended biopsy tool based on the biopsy images illustrating the anatomy of the biopsy site, type of the acquisition tools and the tool operational parameters such as tool position and orientation relative to the biopsy site, among other information.

At 830, the image of the anatomical target and the endoscopic tissue acquisition plan (including the biopsy tool recommendation values of one or more tool operational parameters, and endoscope navigation parameters) generated at 820 may be presented to a user, such as being displayed on a display of a user interface. In some examples, a graphical representation of the navigation of an endoscope based on the navigation parameters and/or a graphical representation of the operation of a biopsy tool based on the tool operational parameters can also be displayed on the user interface.

At 840, a control signal may be provided to an actuator to robotically facilitate operation of a steerable elongate instrument or a biopsy tool associated therewith (such as the recommended biopsy tool) to treat the anatomical target in accordance with the tissue acquisition plan determined at step 820. The steerable elongate instrument can include be a diagnostic or therapeutic endoscope, a cannula, a catheter, a guidewire, or a guide sheath, among others. The actuator can be a motor actuating a robot arm operably coupled to the steerable elongate instrument. The steerable elongate instrument may include a biopsy tool robotically operable via the actuator. In response to the control signal, the actuator can robotically adjust position, posture, direction, and navigation path of the steerable elongate instrument and the biopsy tool included therein, and acquire tissue at the biopsy site in accordance with the navigation parameters and/or the tool operational parameters generated at 820.

Figure 9:
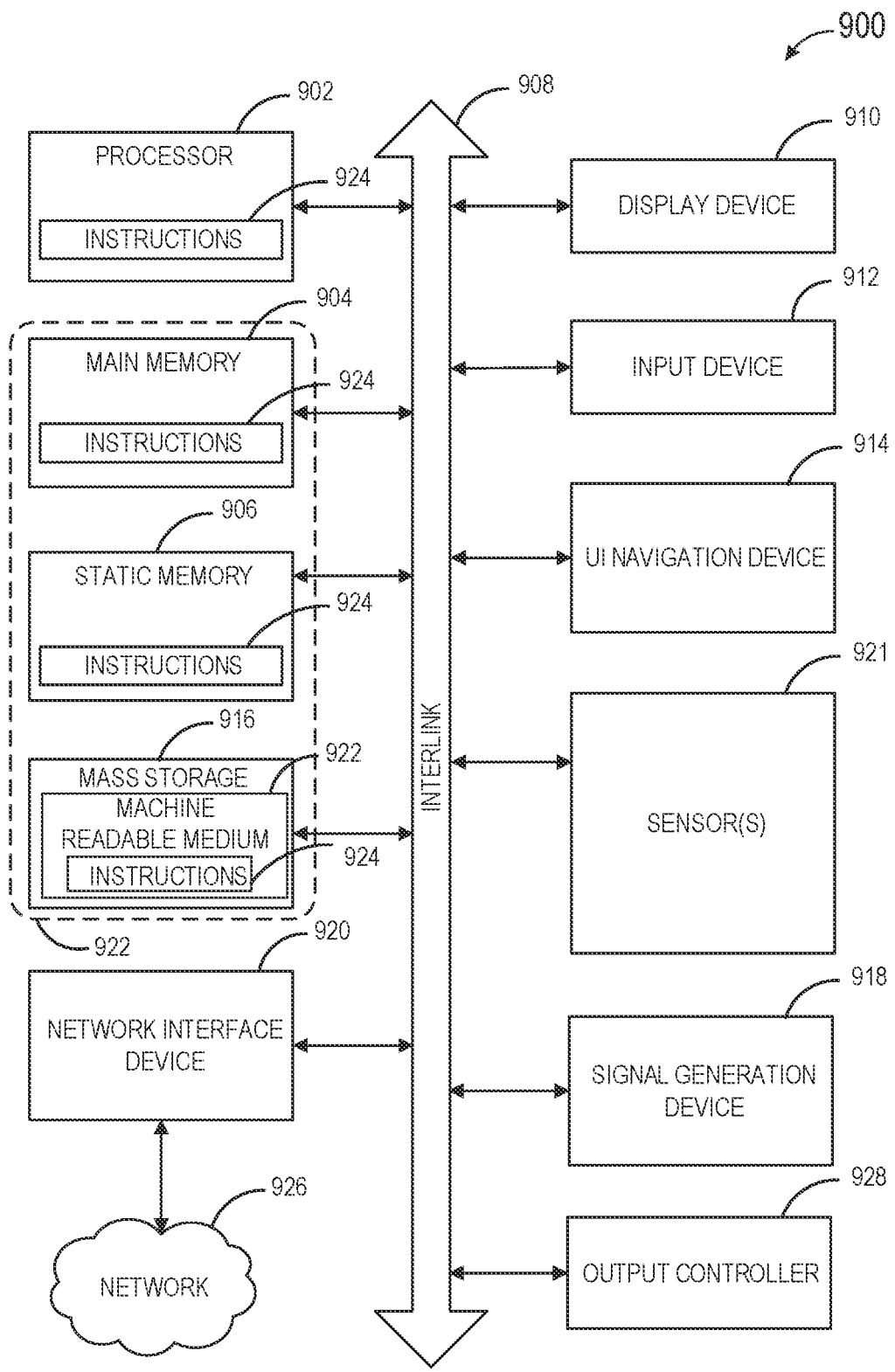
FIG. 9 is a block diagram illustrating an example machine upon which any one or more of the techniques (e.g., methodologies) discussed herein may perform.

FIG. 9 illustrates generally a block diagram of an example machine 900 upon which any one or more of the techniques (e.g., methodologies) discussed herein may perform. Portions of this description may apply to the computing framework of various portions of the endoscopic procedure planning system 600, such as the processor 610 and the device controller 620.

In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a display unit 910 (e.g., a raster display, vector display, holographic display, etc.), an alphanumeric input device 912 (e.g., a keyboard), and a user interface (UI) navigation device 914 (e.g., a mouse). In an example, the display unit 910, input device 912 and UI navigation device 914 may be a touch screen display. The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensors. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 916 may include a machine readable medium 922 on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine-readable medium 922 is illustrated as a single medium, the term "machine readable medium" may include a single medium or multiple media (e.g., a centralized or distributed database, and/or associated caches and servers) configured to store the one or more instructions 924.

The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 924 may further be transmitted or received over a communication network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 920 may include one or more physical jacks (e.g., Ethernet, coaxial, or phone jacks) or one or more antennas to connect to the communication network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

1. An endoscopic system, comprising:
   a steerable elongate instrument configured to be positioned and navigated in a patient anatomy, and to acquire tissue from an anatomical target via a biopsy tool associated with the steerable elongate instrument; and
   a processor configured to:
   receive patient information including an image of the anatomical target;
   apply the received image of the anatomical target to a trained machine-learning (ML) model to generate an endoscopic tissue acquisition plan for acquiring the tissue from the anatomical target; and
   output the generated endoscopic tissue acquisition plan.
2. The endoscopic system of example 1, comprising a user interface configured to present the image of the anatomical target and the generated endoscopic tissue acquisition plan to a user.
3. The endoscopic system of example 2, wherein:
   the user interface is configured to receive a user input designating one or more biopsy locations at the anatomical target; and
   the processor is configured to register the one or more biopsy locations, and to identify one or more biopsied tissues collected therefrom by their respective biopsy locations.
4. The endoscopic system of example 1, comprising a controller configured to provide a control signal to an actuator to robotically facilitate a navigation of the steerable elongate instrument and a manipulation of the biopsy tool to acquire the tissue in accordance with the endoscopic tissue acquisition plan.
5. The endoscopic system of example 1, wherein the processor is configured to use the trained ML model to generate the endoscopic tissue acquisition plan including a recommended biopsy tool of a specific type or size for use in a tissue acquisition procedure.
6. The endoscopic system of example 5, wherein the recommended biopsy tool includes one of a brush, a snare, forceps, or a suction device.
7. The endoscopic system of example 6, wherein the recommended biopsy tool includes a braided snare device sized and shaped to enhance gripping of biopsied tissue.
8. The endoscopic system of example 5, wherein the processor is configured to use the trained ML model to generate the endoscopic tissue acquisition plan including to determine one or more operational parameters for navigating the steerable elongate instrument or maneuvering the recommended biopsy tool to maximize an amount of tissue collected from the anatomical target.
9. The endoscopic system of example 8, wherein the processor is configured to estimate the amount of tissue to be collected by the recommended biopsy tool based on the one or more operational parameters thereof.
10. The endoscopic system of example 8, wherein the determined one or more operational parameters include a position, a posture, a heading direction, or an angle of the biopsy tool relative to the anatomical target.
11. The endoscopic system of example 8, wherein the determined one or more operational parameters include a navigation path for navigating the steerable elongate instrument or maneuvering the recommended biopsy tool to the anatomical target.
12. The endoscopic system of example 1, wherein the processor is configured to use the trained ML model to generate the endoscopic tissue acquisition plan including to determine a recommended amount of tissue to be collected from the anatomical target.
13. The endoscopic system of example 12, wherein the generated endoscopic tissue acquisition plan includes multiple acquisition steps and recommended respective amounts of tissue to be collected at each of the multiple acquisition steps.
14. The endoscopic system of example 1, wherein the processor includes a training module configured to train an ML model using a training dataset comprising procedure data from past endoscopic biopsy procedures on a plurality of patients, the procedure data including (i) images of anatomical targets of the plurality of patients and (ii) assessments of tissue acquisition plans corresponding to the images of anatomical targets.
15. The endoscopic system of example 14, wherein the training module is configured to train the ML model using supervised learning or unsupervised learning.
16. The endoscopic system of example 1, wherein the anatomical target includes an anatomical stricture, and wherein the processor is configured to apply the endoscopic image of the anatomical stricture to the trained ML model to estimate malignancy of the anatomical stricture.
17. A method of planning an endoscopic tissue acquisition procedure for acquiring tissue from an anatomical target via a steerable elongate instrument and a biopsy tool associated therewith, the method comprising:
   providing patient information including an image of the anatomical target;
   applying the image of the anatomical target to a trained machine-learning (ML) model to generate an endoscopic tissue acquisition plan for acquiring tissue from the anatomical target; and outputting the generated endoscopic tissue acquisition plan.
18. The method of example 17, further comprising providing a control signal to an actuator to robotically facilitate a navigation of the steerable elongate instrument and a manipulation of the biopsy tool to acquire the tissue in accordance with the endoscopic tissue acquisition plan.
19. The method of example 17, further comprising:
   receiving a user input designating one or more biopsy locations at the anatomical target;
   registering the one or more biopsy locations; and
   identifying one or more biopsied tissues collected therefrom by their respective biopsy locations.
20. The method of example 17 wherein the generated endoscopic tissue acquisition plan includes a recommended biopsy tool of a specific type or size for use in a tissue acquisition procedure.
21. The method of example 20, wherein the generated endoscopic tissue acquisition plan includes one or more operational parameters for navigating the steerable elongate instrument or maneuvering the recommended biopsy tool to maximize an amount of tissue collected from the anatomical target.
22. The method of example 21, wherein the one or more operational parameters include one or more of:
   a position, a posture, a heading direction, or an angle of the biopsy tool relative to the anatomical target; or
   a navigation path for navigating the steerable elongate instrument or maneuvering the recommended biopsy tool to the anatomical target.

23. The method of example 17, wherein the generated endoscopic tissue acquisition plan includes a recommended amount of tissue to be collected from the anatomical target.

24. The method of example 17, further comprising, via a training module, training an ML model using a training dataset comprising procedure data from past endoscopic biopsy procedures on a plurality of patients, the procedure data including (i) images of anatomical targets of the plurality of patients and (ii) assessments of tissue acquisition plans corresponding to the images of anatomical targets.

25. The method of example 17, wherein the anatomical target includes an anatomical stricture, the method further comprising applying the endoscopic image of the anatomical stricture to the trained ML model to estimate malignancy of the anatomical stricture.

26. A non-transitory machine-readable storage medium that includes instructions that, when executed by one or more processors of a machine, cause the machine to perform operations comprising:

receiving patient information including an image of an anatomical target; applying the image of the anatomical target to a trained machine-learning (ML) model to generate an endoscopic tissue acquisition plan for acquiring tissue from the anatomical target; and outputting the generated endoscopic tissue acquisition plan.

27. The non-transitory machine-readable storage medium of example 26, wherein the instructions cause the machine to perform operations including: receiving a user input designating one or more biopsy locations at the anatomical target;

registering the one or more biopsy locations; and identifying one or more biopsied tissues collected therefrom by their respective biopsy locations.

28. The non-transitory machine-readable storage medium of example 26, wherein the generated endoscopic tissue acquisition plan includes at least one of: a recommended biopsy tool of a specific type or size for use in a tissue acquisition procedure;

one or more operational parameters for navigating a steerable elongate instrument or maneuvering the recommended biopsy tool to maximize an amount of tissue collected from the anatomical target; or a recommended amount of tissue to be collected from the anatomical target.

29. The non-transitory machine-readable storage medium of example 26, wherein the instructions cause the machine to perform operations including training an ML model using a training dataset comprising procedure data from past endoscopic biopsy procedures on a plurality of patients, the procedure data including (i) images of anatomical targets of the plurality of patients and (ii) assessments of tissue acquisition plans corresponding to the images of anatomical targets.

30. The non-transitory machine-readable storage medium of example 26, wherein the instructions cause the machine to perform operations including providing a control signal to an actuator to robotically facilitate a navigation of a steerable elongate instrument and a manipulation of a biopsy tool to acquire the tissue in accordance with the endoscopic tissue acquisition plan.

What is claimed is:

1. A system, configured to be used with a steerable elongate instrument configured to be positioned and navigated in a patient anatomy, and to acquire tissue from an anatomical target via a biopsy tool associated with the steerable elongate instrument, the system comprising:

a processor configured to:

receive patient information including an image of the anatomical target;

receive sensor data indicating a position and a proximity of a distal portion of an endoscope relative to the anatomical target;

receive procedure data including one or more operational parameters associated with the steerable elongate instrument or the biopsy tool;

apply the received image of the anatomical target, the received sensor data, and the received procedure data to a trained machine-learning (ML) model to generate an endoscopic tissue acquisition plan for acquiring the tissue from the anatomical target, wherein the endoscopic tissue acquisition plan includes:

an analysis of one or more characteristics of the anatomical target based on the received image, the received sensor data, and the received procedure data, wherein the one or more characteristics include one or more of a location of the anatomical target, a size of the anatomical target, or a shape of the anatomical target;

an identified biopsy acquisition site, wherein the identified biopsy acquisition site includes the anatomical target; and multiple tissue acquisition steps for acquiring tissue at the biopsy acquisition site with a recommended amount of tissue to be collected at each step; and output the generated endoscopic tissue acquisition plan.

2. The system of claim 1, comprising a user interface configured to present the image of the anatomical target and the generated endoscopic tissue acquisition plan to a user.

3. The system of claim 2, wherein:

the user interface is configured to receive a user input designating one or more biopsy locations at the anatomical target; and the processor is configured to register the one or more biopsy locations, and to identify one or more biopsied tissues collected therefrom by their respective biopsy locations.

4. The system of claim 1, comprising a controller configured to provide a control signal to an actuator to robotically facilitate a navigation of the steerable elongate instrument and a manipulation of the biopsy tool to acquire the tissue in accordance with the endoscopic tissue acquisition plan.

5. The system of claim 1, wherein the processor is configured to use the trained ML model to generate the endoscopic tissue acquisition plan including a recommended biopsy tool of a specific type or size for use in a tissue acquisition procedure.

6. The system of claim 5, wherein the recommended biopsy tool includes one of a brush, a snare, forceps, or a suction device.

7. The system of claim 6, wherein the recommended biopsy tool includes a braided snare device sized and shaped to enhance gripping of biopsied tissue.

8. The system of claim 5, wherein the one or more operational parameters include parameters for navigating the steerable elongate instrument or maneuvering the recommended biopsy tool to maximize an amount of tissue collected from the anatomical target.

9. The system of claim 8, wherein the processor is configured to estimate the amount of tissue to be collected by the recommended biopsy tool based on the one or more operational parameters thereof.

10. The system of claim 8, wherein the one or more operational parameters include a position, a posture, a heading direction, or an angle of the biopsy tool relative to the anatomical target.

11. The system of claim 8, wherein the one or more operational parameters include a navigation path for navigating the steerable elongate instrument or maneuvering the recommended biopsy tool to the anatomical target.

12. The system of claim 1, wherein the processor is configured to use the trained ML model to generate the endoscopic tissue acquisition plan including to determine a recommended amount of tissue to be collected from the anatomical target.

13. The system of claim 1, wherein the processor includes a training module configured to train an ML model using a training dataset comprising procedure data from past endoscopic biopsy procedures on a plurality of patients, the procedure data including (i) images of anatomical targets of the plurality of patients and (ii) assessments of tissue acquisition plans corresponding to the images of anatomical targets.

14. The system of claim 13, wherein the training module is configured to train the ML model using supervised learning or unsupervised learning.

15. The system of claim 1, wherein the anatomical target includes an anatomical stricture, and wherein the processor is configured to apply the image of the anatomical stricture to the trained ML model to estimate malignancy of the anatomical stricture.

16. A method of planning an endoscopic tissue acquisition procedure for acquiring tissue from an anatomical target via a steerable elongate instrument and a biopsy tool associated therewith, the method comprising:
   providing patient information including an image of the anatomical target;
   receiving sensor data indicating a position and a proximity of a distal portion of an endoscope relative to the anatomical target;
   receiving procedure data including one or more operational parameters associated with the biopsy tool;
   applying the image of the anatomical target, the received sensor data, and the received procedure data to a trained machine-learning (ML) model to generate an endoscopic tissue acquisition plan for acquiring tissue from the anatomical target, wherein the tissue acquisition plan includes:
      an analysis of one or more characteristics of the anatomical target based on the received image, the received sensor data, and the received procedure data, wherein the one or more characteristics include one or more of, a location of the anatomical target, a size of the anatomical target, or a shape of the anatomical target;
      an identified biopsy acquisition site, wherein the identified biopsy acquisition site includes the anatomical target; and
      multiple acquisition steps for acquiring tissue at the biopsy acquisition site with a recommended amount of tissue to be collected at each site; and
   outputting the generated endoscopic tissue acquisition plan.

17. The method of claim 16, further comprising:
   receiving a user input designating one or more biopsy locations at the anatomical target;
   registering the one or more biopsy locations; and
   identifying one or more biopsied tissues collected therefrom by their respective biopsy locations.

18. The method of claim 16, wherein the generated endoscopic tissue acquisition plan includes a recommended biopsy tool of a specific type or size for use in a tissue acquisition procedure.

19. The method of claim 16, further comprising, via a training module, training an ML model using a training dataset comprising procedure data from past endoscopic biopsy procedures on a plurality of patients, the procedure data including (i) images of anatomical targets of the plurality of patients and (ii) assessments of tissue acquisition plans corresponding to the images of anatomical targets.

20. The system of claim 1, wherein the processor is further configured to:
   receive additional patient information including i) external imaging data of the anatomical target and a location proximate to the anatomical target including at least one of x-ray, fluoroscopy, a computer tomography (CT) image, a magnetic resonance imaging (MRI) image, or an ultrasound image, and ii) patient medical information including a tissue inflammation state and general health status;
   apply the external imaging data of the anatomical target and the patient medical information to the trained machine-learning (ML) model to:
      analyze, based on the image of the anatomical target and the external imaging data, multiple characteristics of the anatomical target, wherein the multiple characteristics includes a size of the anatomical target, a location of the anatomical target, and a neighboring anatomical environment proximate to the anatomical target;
      determine a recommended biopsy tool of a specific side and type based on the analyzed multiple characteristics, the patient medical information, the additional patient information, and one or more local conditions at a surgical site including the anatomical target and the neighboring anatomical environment; and
      update the endoscopic tissue acquisition plan to include the recommended biopsy tool for use in a tissue acquisition procedure; and
   output the updated endoscopic tissue acquisition plan.

* * * * *